US008802122B2

(12) United States Patent
Lu et al.

(10) Patent No.: US 8,802,122 B2
(45) Date of Patent: *Aug. 12, 2014

(54) MULTI-PHASED, BIODEGRADABLE AND OSTEOINTEGRATIVE COMPOSITE SCAFFOLD FOR BIOLOGICAL FIXATION OF MUSCULOSKELETAL SOFT TISSUE OF BONE

(75) Inventors: Helen H. Lu, New York, NY (US); Jeffrey Spalazzi, Staten Island, NY (US); Kathie Dionisio, N. Andover, MA (US)

(73) Assignee: The Trustees of Columbia University in the City of New York, New York, NY (US)

( * ) Notice: Subject to any disclaimer, the term of this patent is extended or adjusted under 35 U.S.C. 154(b) by 976 days.

This patent is subject to a terminal disclaimer.

(21) Appl. No.: 12/655,193

(22) Filed: Dec. 22, 2009

(65) Prior Publication Data

US 2010/0291178 A1 Nov. 18, 2010

Related U.S. Application Data

(63) Continuation of application No. 11/073,275, filed on Mar. 4, 2005, now Pat. No. 7,767,221.

(60) Provisional application No. 60/550,700, filed on Mar. 5, 2004.

(51) Int. Cl.
*A61F 2/02* (2006.01)

(52) U.S. Cl.
USPC .......................... 424/423; 623/11.11

(58) Field of Classification Search
None
See application file for complete search history.

(56) References Cited

U.S. PATENT DOCUMENTS

| 4,479,271 | A | * | 10/1984 | Bolesky et al. ............ 623/20.17 |
|---|---|---|---|---|
| 5,108,436 | A | | 4/1992 | Chu et al. |
| 5,133,755 | A | | 7/1992 | Brekke |
| 5,366,508 | A | | 11/1994 | Brekke |
| 5,607,474 | A | | 3/1997 | Athanasiou et al. |
| 5,626,861 | A | | 5/1997 | Laurencin et al. |
| 5,683,459 | A | | 11/1997 | Brekke |
| 5,716,413 | A | | 2/1998 | Walter et al. |
| 5,755,792 | A | | 5/1998 | Brekke |
| 5,766,618 | A | | 6/1998 | Laurencin et al. |
| 5,849,331 | A | | 12/1998 | Ducheyne et al. |
| 5,855,610 | A | | 1/1999 | Vacanti et al. |
| 5,866,155 | A | | 2/1999 | Laurencin et al. |
| 5,904,717 | A | | 5/1999 | Brekke et al. |
| 5,922,025 | A | | 7/1999 | Hubbard |
| 5,944,754 | A | | 8/1999 | Vacanti |
| 6,005,161 | A | | 12/1999 | Brekke et al. |
| 6,013,591 | A | | 1/2000 | Ying et al. |
| 6,143,293 | A | | 11/2000 | Weiss et al. |
| 6,179,878 | B1 | | 1/2001 | Duerig et al. |
| 6,187,329 | B1 | | 2/2001 | Agrawal et al. |
| 6,187,742 | B1 | | 2/2001 | Wozney et al. |
| 6,235,061 | B1 | | 5/2001 | Laurencin et al. |
| 6,291,547 | B1 | | 9/2001 | Lyles et al. |
| 6,306,424 | B1 | | 10/2001 | Vyakarnam et al. |
| 6,328,765 | B1 | | 12/2001 | Hardwick et al. |
| 6,333,029 | B1 | | 12/2001 | Vyakarnam et al. |
| 6,365,149 | B2 | | 4/2002 | Vyakarnam et al. |
| 6,378,527 | B1 | | 4/2002 | Hungerford et al. |
| 6,432,437 | B1 | | 8/2002 | Hubbard |
| 6,454,811 | B1 | | 9/2002 | Sherwood et al. |
| 6,459,948 | B1 | | 10/2002 | Ateshian et al. |
| 6,534,084 | B1 | | 3/2003 | Vyakarnam et al. |
| 6,541,022 | B1 | | 4/2003 | Murphy et al. |
| 6,544,503 | B1 | | 4/2003 | Vanderhoff et al. |
| 6,558,612 | B1 | | 5/2003 | Hubbard |
| 6,579,533 | B1 | | 6/2003 | Tormala et al. |
| 6,602,294 | B1 | | 8/2003 | Sittinger et al. |
| 6,626,950 | B2 | | 9/2003 | Brown et al. |
| 6,730,252 | B1 | | 5/2004 | Teoh et al. |
| 6,787,518 | B1 | | 9/2004 | Kato et al. |
| 6,852,330 | B2 | | 2/2005 | Bowman et al. |
| 6,984,623 | B2 | | 1/2006 | Celeste et al. |
| 7,087,200 | B2 | | 8/2006 | Taboas et al. |
| 7,112,417 | B2 | | 9/2006 | Vyakarnam et al. |
| 7,217,294 | B2 | | 5/2007 | Kusanagi et al. |
| 7,252,685 | B2 | | 8/2007 | Bindseil et al. |
| 7,319,035 | B2 | | 1/2008 | Vacanti et al. |
| 7,326,426 | B2 | | 2/2008 | Nathan et al. |
| 7,351,250 | B2 | | 4/2008 | Zamierowski |
| 7,390,526 | B2 | | 6/2008 | Stupp et al. |
| 7,419,681 | B2 | | 9/2008 | Tormala et al. |

(Continued)

FOREIGN PATENT DOCUMENTS

| JP | 6-154305 | 6/1994 |
|---|---|---|
| JP | 6-165817 | 6/1994 |

(Continued)

OTHER PUBLICATIONS

U.S. Appl. No. 12/455,765, filed Jun. 6, 2009, Lu et al.
U.S. Appl. No. 12/583,072, filed Aug. 12, 2009, Lu et al.
Office Action issued Oct. 18, 2007 by the U.S. Patent and Trademark Office in connection with U.S. Appl. No. 11/073,261.
Final Office Action issued Apr. 30, 2008 by the U.S. Patent and Trademark Office in connection with U.S. Appl. No. 11/073,261.
Office Action issued Aug. 28, 2008 by the U.S. Patent and Trademark Office in connection with U.S. Appl. No. 11/073,261.
Final Office Action issued Mar. 6, 2009 by the U.S. Patent and Trademark Office in connection with U.S. Appl. No. 11/073,261.
PCT International Preliminary Report on Patentability issued Feb. 24, 2009 in connection with PCT Application No. PCT/US2005/007010, int'l filing date Mar. 4, 2005.

(Continued)

*Primary Examiner* — Anand Desai

(74) *Attorney, Agent, or Firm* — John P. White; Cooper & Dunham LLP

(57) ABSTRACT

Methods and apparatuses are provided for musculoskeletal tissue engineering. For example, a scaffold apparatus is provided which comprises microspheres of selected sizes and/or composition. The microspheres are layered to have a gradient of microsphere sizes and/or compositions. The scaffold provides a functional interface between multiple tissue types.

13 Claims, 23 Drawing Sheets

(56) References Cited

U.S. PATENT DOCUMENTS

| | | | |
|---|---|---|---|
| 7,524,335 B2 | 4/2009 | Slivka et al. | |
| 7,704,740 B2 | 4/2010 | Schindler et al. | |
| 7,767,221 B2* | 8/2010 | Lu et al. | 424/423 |
| 7,786,086 B2 | 8/2010 | Reches et al. | |
| 7,803,574 B2 | 9/2010 | Desai et al. | |
| 7,842,737 B2 | 11/2010 | Wang et al. | |
| 7,901,461 B2 | 3/2011 | Harmon et al. | |
| 8,142,501 B2 | 3/2012 | Macossay-Torres | |
| 8,168,431 B2 | 5/2012 | Brady et al. | |
| 8,187,326 B2 | 5/2012 | Hammer et al. | |
| 8,226,715 B2 | 7/2012 | Hwang et al. | |
| 2001/0000195 A1 | 4/2001 | Smith et al. | |
| 2002/0095213 A1 | 7/2002 | Bakker et al. | |
| 2002/0119177 A1 | 8/2002 | Bowman et al. | |
| 2002/0127265 A1 | 9/2002 | Bowman et al. | |
| 2002/0182241 A1 | 12/2002 | Borenstein et al. | |
| 2002/0187104 A1 | 12/2002 | Li et al. | |
| 2003/0004578 A1 | 1/2003 | Brown et al. | |
| 2003/0071380 A1 | 4/2003 | Wang et al. | |
| 2003/0114936 A1 | 6/2003 | Sherwood et al. | |
| 2003/0147935 A1 | 8/2003 | Binette et al. | |
| 2003/0175257 A1 | 9/2003 | Song et al. | |
| 2003/0225459 A1 | 12/2003 | Hammer et al. | |
| 2004/0010320 A1 | 1/2004 | Huckle et al. | |
| 2004/0033214 A1 | 2/2004 | Young et al. | |
| 2004/0078090 A1 | 4/2004 | Binette et al. | |
| 2004/0109845 A1 | 6/2004 | Terkeltaub | |
| 2004/0122209 A1 | 6/2004 | Poole | |
| 2004/0243235 A1 | 12/2004 | Goh et al. | |
| 2005/0008675 A1 | 1/2005 | Bhatia et al. | |
| 2005/0095695 A1 | 5/2005 | Shindler et al. | |
| 2005/0118236 A1 | 6/2005 | Qiu et al. | |
| 2005/0196425 A1 | 9/2005 | Zamora et al. | |
| 2005/0205498 A1 | 9/2005 | Sowemimo-Coker et al. | |
| 2005/0255583 A1 | 11/2005 | Depaola et al. | |
| 2006/0036331 A1 | 2/2006 | Lu et al. | |
| 2006/0067969 A1 | 3/2006 | Lu et al. | |
| 2006/0165663 A1 | 7/2006 | Tanaka et al. | |
| 2006/0204738 A1 | 9/2006 | Dubrow et al. | |
| 2006/0273279 A1 | 12/2006 | Kaplan et al. | |
| 2007/0269481 A1 | 11/2007 | Li et al. | |
| 2008/0026419 A1 | 1/2008 | Bottlang et al. | |
| 2008/0044900 A1 | 2/2008 | Mooney et al. | |
| 2008/0170982 A1 | 7/2008 | Zhang et al. | |
| 2008/0274545 A1 | 11/2008 | Kuo et al. | |
| 2009/0162643 A1 | 6/2009 | Dubrow et al. | |
| 2009/0196901 A1 | 8/2009 | Guilak et al. | |
| 2009/0317446 A1 | 12/2009 | Tan et al. | |
| 2010/0168771 A1 | 7/2010 | Guldberg et al. | |
| 2010/0172952 A1 | 7/2010 | Srouji et al. | |
| 2010/0179659 A1 | 7/2010 | Li et al. | |
| 2010/0234955 A1 | 9/2010 | Santerre et al. | |
| 2010/0303881 A1 | 12/2010 | Hoke et al. | |
| 2010/0331979 A1 | 12/2010 | McDade et al. | |
| 2011/0020917 A1 | 1/2011 | Wen et al. | |
| 2011/0066242 A1 | 3/2011 | Lu et al. | |
| 2011/0201984 A1 | 8/2011 | Dubrow et al. | |
| 2011/0293685 A1 | 12/2011 | Kuo et al. | |
| 2012/0046758 A1 | 2/2012 | Evans et al. | |

FOREIGN PATENT DOCUMENTS

| | | |
|---|---|---|
| WO | WO 98/22041 | 5/1998 |
| WO | WO/99/07777 | 2/1999 |
| WO | WO/99/33415 | 7/1999 |
| WO | WO 01/34060 | 5/2001 |
| WO | WO/2005/089127 | 9/2005 |
| WO | WO/2008/070186 | 6/2008 |
| WO | WO 2008/091391 | 7/2008 |
| WO | WO/2008/100534 | 8/2008 |
| WO | WO 2008/128304 | 10/2008 |
| WO | WO/2008/154030 | 12/2008 |
| WO | WO/2008/154035 | 12/2008 |
| WO | WO/2008/156725 | 12/2008 |
| WO | WO/2009/038808 | 3/2009 |
| WO | WO 2009/102967 | 8/2009 |
| WO | WO 2010/144992 | 12/2010 |
| WO | WO 2011/163328 | 12/2011 |
| WO | WO 2012/009341 | 1/2012 |
| WO | WO 2012/021885 | 2/2012 |

OTHER PUBLICATIONS

PCT International Preliminary Report on Patentability issued Sep. 5, 2006 in connection with PCT Application No. PCT/US2005/007129, int'l filing date Mar. 4, 2005.

PCT International Preliminary Report on Patentability issued Jun. 10, 2009 in connection with PCT Application No. PCT/US2007/025127, int'l filing date Dec. 6, 2007.

PCT International Search Report issued on Dec. 8, 2008 in connection with PCT Application No. PCT/US2008/007323, international filing date Jun. 11, 2008.

PCT International Search Report issued on Feb. 14, 2006 in connection with PCT Application No. PCT/US2005/007129, international filing date Mar. 4, 2005.

PCT International Search Report issued on Jan. 6, 2009 in connection with PCT Application No. PCT/US2008/010985, international filing date Sep. 22, 2008.

PCT International Search Report issued on Jul. 14, 2008 in connection with PCT Application No. PCT/US05/07010, international filing date Mar. 4, 2005.

PCT International Search Report issued on Jul. 19, 2008 in connection with PCT Application No. PCT/US08/01889, international filing date Feb. 12, 2008.

PCT International Search Report issued on Jun. 17, 2008 in connection with PCT Application No. PCT/US2007/025127, international filing date Dec. 6, 2007.

PCT International Search Report issued on Mar. 3, 2009 in connection with PCT Application No. PCT/US2008/007485, international filing date Jun. 11, 2008.

PCT International Search Report issued on Oct. 14, 2008 in connection with PCT Application No. PCT/US2008/07357, international filing date Jun. 11, 2008.

Written Opinion of the International Search Authority dated Feb. 14, 2006, in connection with PCT/US2005/007129, international filing date Mar. 4, 2005.

Written Opinion of the International Search Authority dated Jan. 6, 2009, in connection with PCT/US2008/010985, international filing date Sep. 22, 2008.

Written Opinion of the ISA dated Jul. 14, 2008 in connection with International Application No. PCT/US05/07010, international filing date Mar. 4, 2005.

Written Opinion of the ISA dated Jun. 17, 2008 in connection with International Application No. PCT/US2007/025127, international filing date Dec. 6, 2007.

Brooks, Peter (2002) "Impact of Osteoarthritis on Individuals and Society . . . Implications" Curr. Opin. in Rheumatology. 14(5):573-577.

Lu et al. (2001) "Polymer-bioactive glass composite . . . evaluations." BED 50:693-694 (ASME Proceedings of the Bioengineering Conference, 2001).

Lu et al. (2003) "Three-dimensional, bioactive, . . . in vitro" J. Biomed. Matls. Res. Part A 64(3):465-474.

Mikos, et al. (2006) "Engineering Complex Tissues" Tissue Engineering 12 (12):3307-3339.

Sherwood et al. (2002) "A three-dimensional osteocondral composite scaffold for articular cartilage repair." Biomaterials 23: 4739-4751.

Spalazzi et al. (2003) "Osteoblast and Chondrocyte . . . n Scaffolds." IEEE Engineering in Medicine and Biology Magazine Sep./Oct. 2003: 27-34.

Spalazzi, et al. (2006) "Development of Controlled Matrix Heterogeneity on a Triphasic Scaffold for Orthopedic Interface Tissue Engineering" Tissue Eng. 12(12):3497-508.

Spalazzi JP, et al. (2008) "Mechanoactive Scaffold Induces Tendon Remodeling and Expression of Fibrocartilage Markers" clin orthop relat res 466:1938-1948.

Stys, PK (2005) "General mechanisms of axonal damage and its prevention." J. Neurol. Sci. 233: 3-13.

(56) References Cited

OTHER PUBLICATIONS

Xie J, et al. (2006) "Mechano-active scaffold design . . . mechanical behaviors" Tissue Eng. 12(3):449-58.
Yoshimoto et al. (2003) "A biodegradable nanofiber scaffold by electrospinning and its potential for bone tissue engineering." Biomaterials 24: 2077-2082.
PCT International Preliminary Report on Patentability issued on Dec. 11, 2009 in connection with PCT App. No. PCT/US2008/007323, International Filing Date Jun. 11, 2008.
PCT International Preliminary Report on Patentability issued on Dec. 11, 2009 in connection with PCT App. No. PCT/US2008/007357, International Filing Date Jun. 11, 2008.
PCT International Search Report issued on Feb. 17, 2010 in connection with PCT Application No. PCT/US09/06453, International Filing Date Dec. 8, 2009.
Written Opinion of the International Search Authority dated Jan. 2, 2009, in connec. with International App. No. PCT/US2008/007323, International Filing Date Jun. 11, 2008.
Written Opinion of the International Search Authority dated Feb. 17, 2010, in connec. with International App. No. PCT/US09/06453 International Filing Date Dec. 8, 2009.
Written Opinion of the International Search Authority dated Oct. 14, 2008, in connec. with International App. No. PCT/US2008107357, International Filing Date Jun. 11, 2008.
Office Action issued Oct. 4, 2007 by the U.S. Patent and Trademark Office in connection with U.S. Appl. No. 11/073,275.
Office Action issued Apr. 17, 2008 by the U.S. Patent and Trademark Office in connection with U.S. Appl. No. 11/073,275.
Final Office Action issued Nov. 13, 2008 by the U.S. Patent and Trademark Office in connection with U.S. Appl. No. 11/073,275.
Notice of Allowance issued May 14, 2009 by the U.S. Patent and Trademark Office in connection with U.S. Appl. No. 11/073,275.
Notice of Allowance issued Sep. 24, 2009 by the U.S. Patent and Trademark Office in connection with U.S. Appl. No. 11/073,275.
Kwei, et al. (2010) "Nanofiber Alignment Regulates Adhesion and . . . " Bioengineering Conference—Proceedings of the 2010 IEEE 36th Annual Northeast, Mar. 26-28, 2010, pp. 1-2.
Leong, et al. (2006) "Polymer-Ceramic Composite Scaffold Induces . . . " Proceedings of the 28th IEEE EMBS Annual International Conference. Aug. 30-Sep. 3, pp. 2651-2654.
Thibault, et al. (2010) "Osteogenic Differentiation of Mesenchymal Stem Cells on . . . ". Tissue Engineering: Part A. 16(2):431-440.
Yin et al. (2009) "The Regulation of Tendon Stem Cell Differentiation by the Alignment of Nanofibers" Biomaterials. 31:2163-2175.
PCT International Search Report issued on Jan. 5, 2012 in connection with PCT International Application No. PCT/US11/47739.
PCT International Search Report issued on Jan. 9, 2012 in connection with PCT International Application No. PCT/US11/41391.
PCT International Search Report issued on Jan. 9, 2012 in connection with PCT International Application No. PCT/US11/43687.
Written Opinion of the International Search Authority dated Jan. 5, 2012 in connection with PCT International Application No. PCT/US11/47739.
Written Opinion of the International Search Authority dated Jan. 9, 2012 in connection with PCT International Application No. PCT/US11/41391.
Written Opinion of the International Search Authority dated Jan. 9, 2012 in connection with PCT International Application No. PCT/US11/43687.
Mar. 16, 2012 Office Action issued in connection with U.S. Appl. No. 12/583,072.
Jun. 18, 2012 Response to Mar. 16, 2012 Office Action filed in connection with U.S. Appl. No. 12/583,072.
Nov. 9, 2012 Final Office Action issued in connection with U.S. Appl. No. 12/583,072.
Mar. 11, 2013 Response to Nov. 9, 2012 Final Office Action filed in connection with U.S. Appl. No. 12/583,072.
Mar. 25, 2013 Advisory Action issued in connection with U.S. Appl. No. 12/583,072.
Apr. 9, 2013 Response to Nov. 9, 2012 Final Office Action and Mar. 25, 2013 Advisory Action as a Submission Accompanying a RCE filed in connection with U.S. Appl. No. 12/583,072.
Apr. 29, 2013 Office Action issued in connection with U.S. Appl. No. 12/583,072.
Jan. 24, 2012 Office Action issued in connection with U.S. Appl. No. 12/806,912.
May 9, 2012 Response to Jan. 24, 2012 Office Action filed in connection with U.S. Appl. No. 12/806,912.
Aug. 3, 2012 Office Action issued in connection with U.S. Appl. No. 12/806,912.
Dec. 3, 2012 Amendment in Response to Aug. 3, 2012 Office Action filed in connection with U.S. Appl. No. 12/806,912.
Feb. 5, 2013 Final Office Action issued in connection with U.S. Appl. No. 12/806,912.
Apr. 5, 2013 Response to Feb. 5, 2013 Final Office Action filed in connection with U.S. Appl. No. 12/806,912.
Apr. 18, 2011 Office Action issued in connection with U.S. Appl. No. 12/455,765.
Jun. 7, 2011 Response to Apr. 18, 2011 Office Action issued in connection with U.S. Appl. No. 12/455,765.
Sep. 8, 2011 Office Action issued in connection with U.S. Appl. No. 12/455,765.
Feb. 8, 2012 Response to Sep. 8, 2011 Office Action issued in connection with U.S. Appl. No. 12/455,765.
Oct. 18, 2012 Extended European Search Report issued in connection with European Application No. 08768402.3.
Nov. 18, 2011 Communication Pursuant to Article 94(3) EPC issued in connection with European Application No. 05724636.5.
Mar. 23, 2013 Response to Nov. 18, 2011 Communication Pursuant to Article 94(3) EPC filed in connection with European Application No. 05724636.5.
Dec. 15, 2011 Office Action issued in connection with Canadian Application No. 2,557,231.

* cited by examiner

Figure 1A
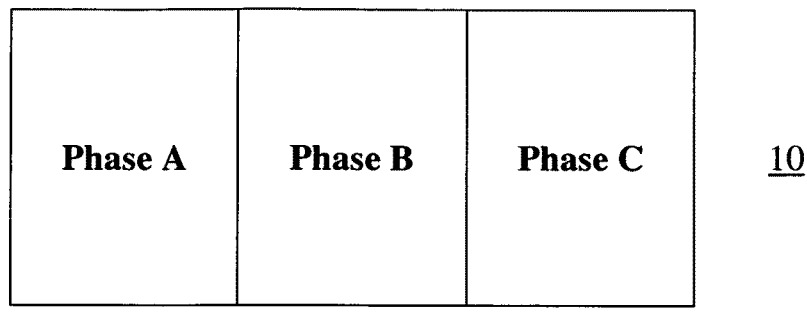
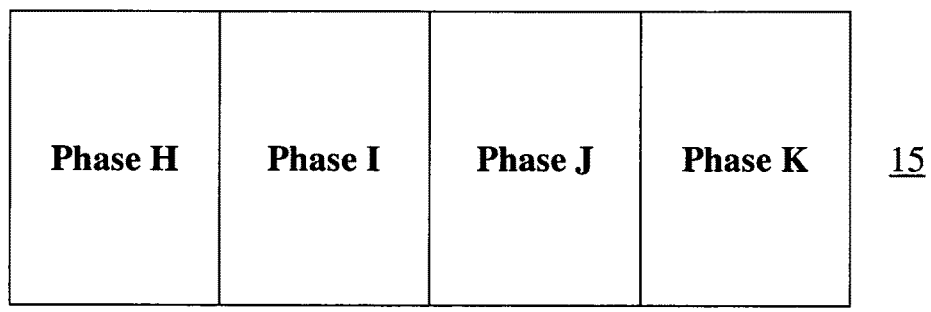
Figure 1B
Figure 2
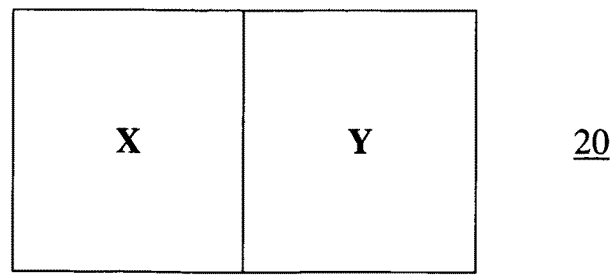

Figure 3
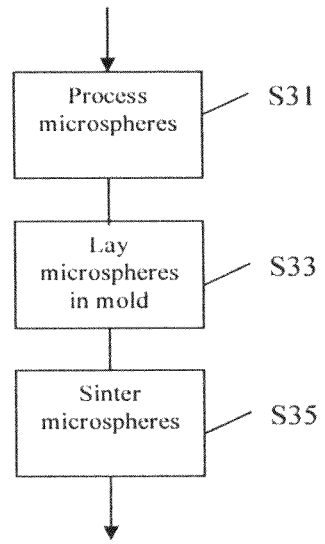
Figure 4A
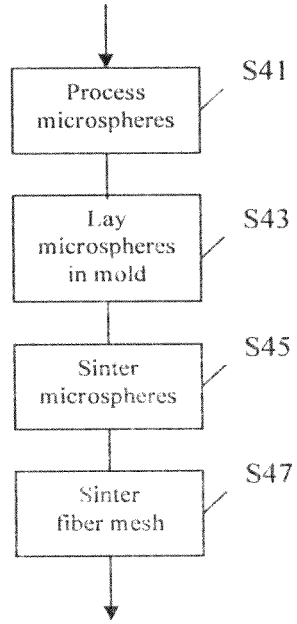
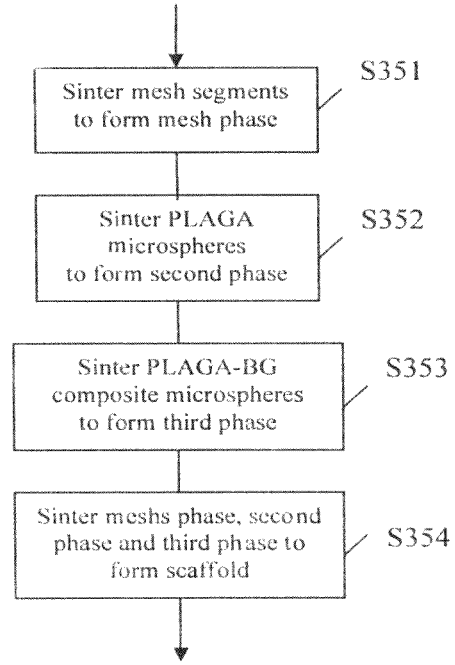
Figure 4B

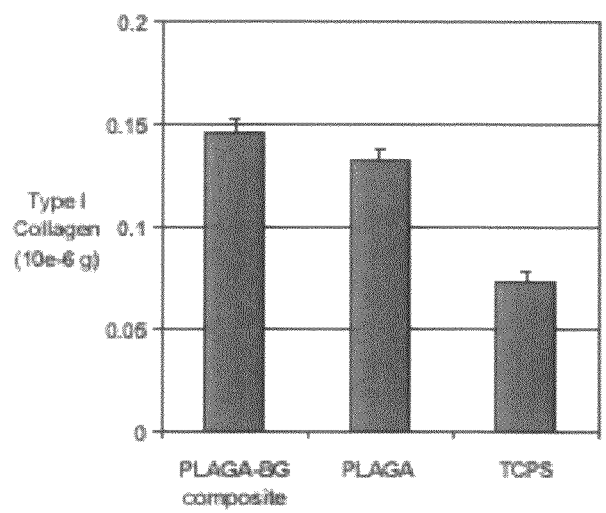
Figure 14
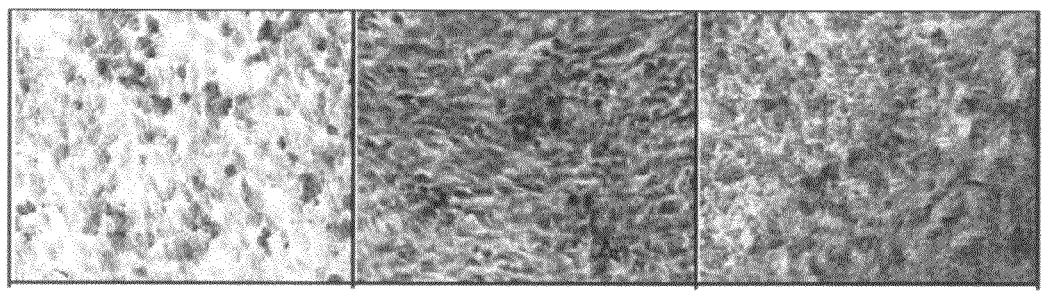
| Figure 15A | Figure 15B | Figure 15C |
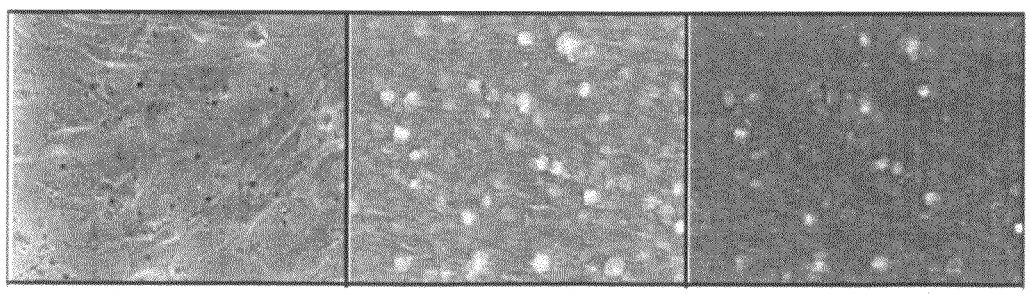
| Figure 16A | Figure 16B | Figure 16C |

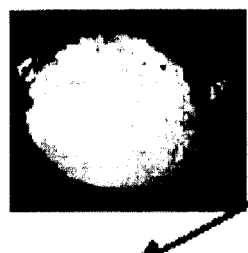 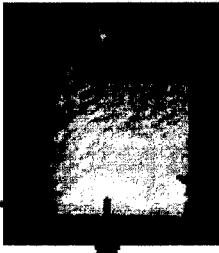 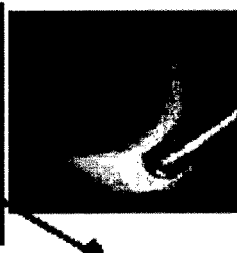
Figure 17A  Figure 17B  Figure 17C
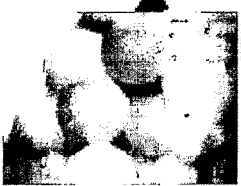  
Figure 17D  Figure 17E  Figure 17F
 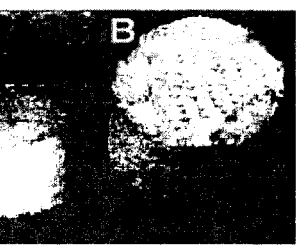 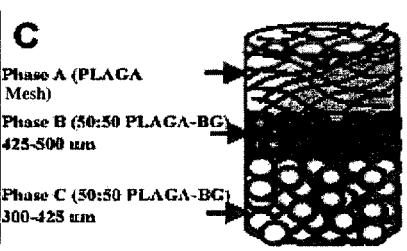
Figure 18A  Figure 18B  Figure 18C

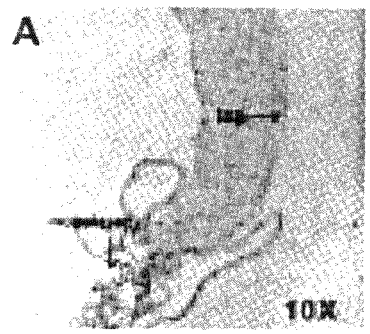
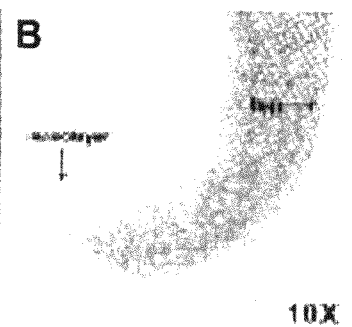
Figure 19A  Figure 19B
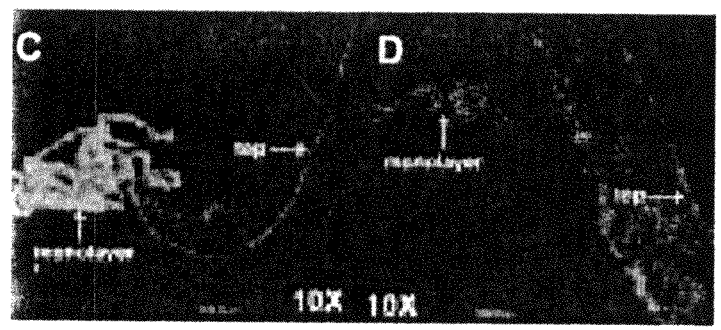
Figure 19C  Figure 19D
Figure 20A
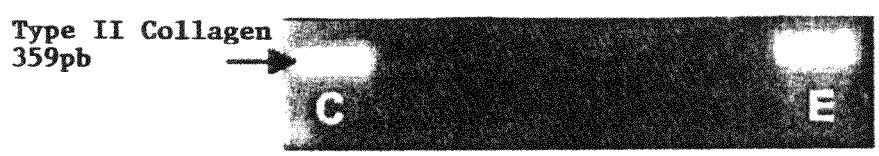
Figure 20B

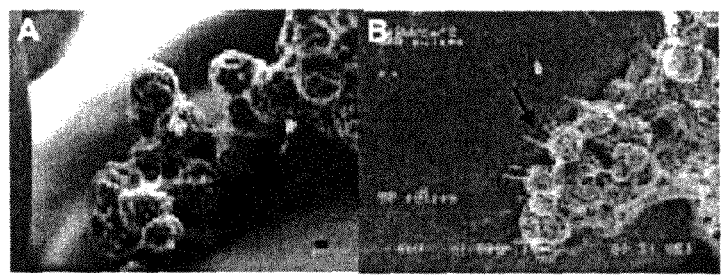
Figure 21A    Figure 21B
Figure 22A    Figure 22B    Figure 22C
Figure 23
| Scaffold Type | Average Porosity | Pore Diameter | Elastic Modulus (MPa) | Compressive Strength (MPa) |
|---|---|---|---|---|
| PLAGA | 31% | 116 μm | 26.48 ± 3.47 | 0.53 ± 0.07 |
| PLAGA-BG | 43% | 89 μm | 51.34 ± 6.08 | 0.42 ± 0.05 |

|  | Intrusion Volume (μL) | Porosity (%) | Mode Pore Diam. (μm) |
|---|---|---|---|
| Phase A | 41±8 | 58±5 | 73±11 |
| Phase B | 28±7 | 34±4 | 75±7 |
| Phase C | 12.5 | 25.7 | 83 |
FIG. 28-1
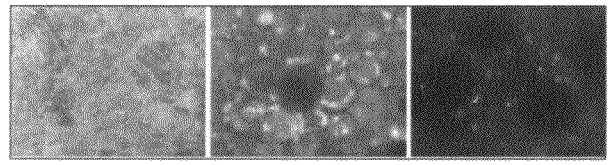
FIG. 28-2A    FIG. 28-2B    FIG. 28-2C
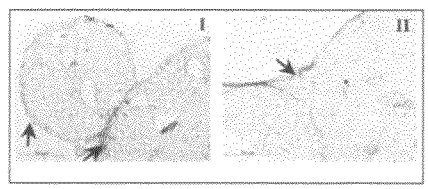
FIG. 28-3A    FIG. 28-3B FIG. 29-1A    FIG. 29-1B
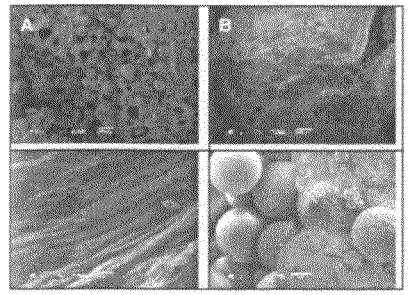
FIG. 29-1C    FIG. 29-1D
FIG. 29-2A    FIG. 29-2B    FIG. 29-2C
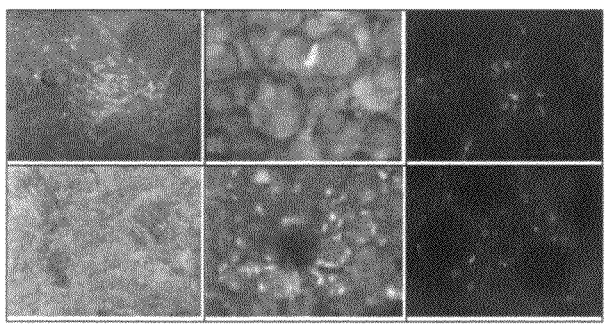
FIG. 29-2D    FIG. 29-2E    FIG. 29-2F
FIG. 29-3A1    FIG. 29-3A2    FIG. 29-3A3
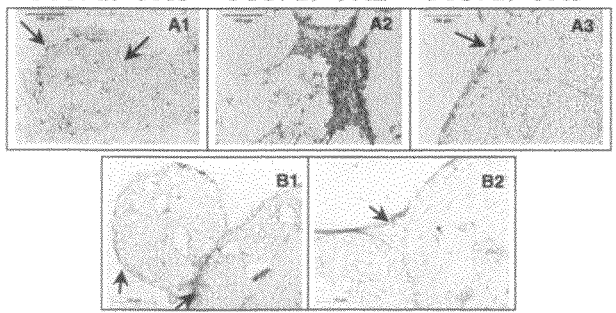
FIG. 29-3B1    FIG. 29-3B2
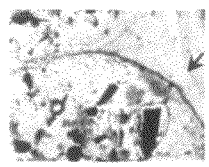
FIG. 29-3C FIG. 31-1
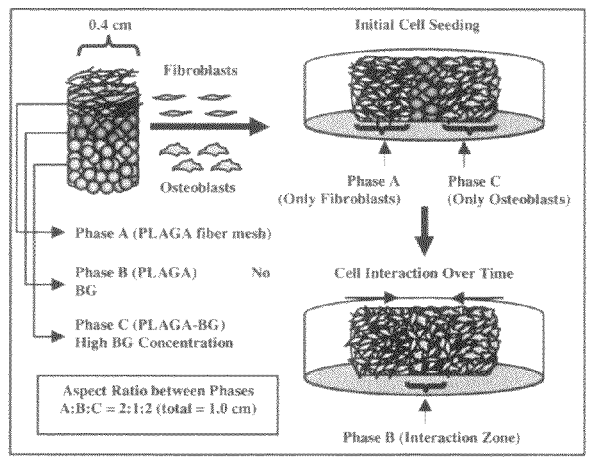
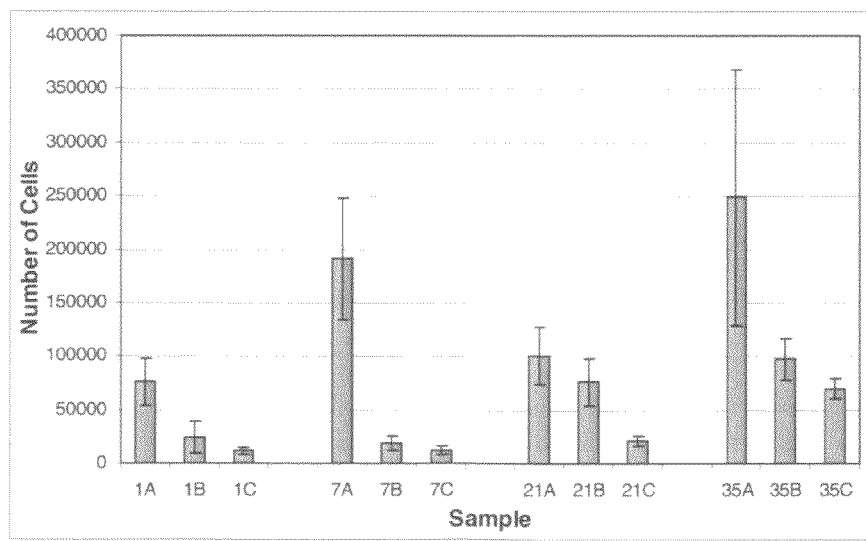
FIG. 31-2

FIG. 31-3A
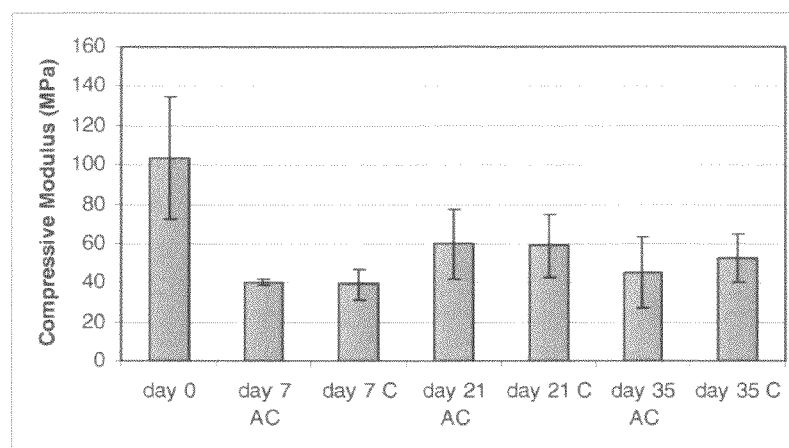
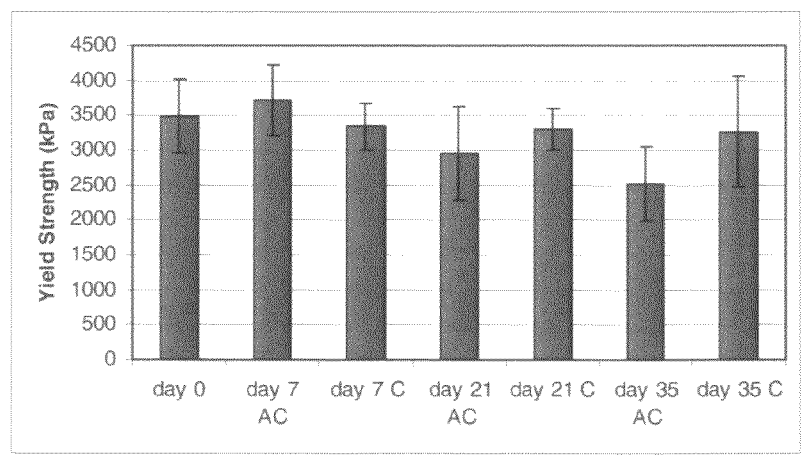
FIG. 31-3B

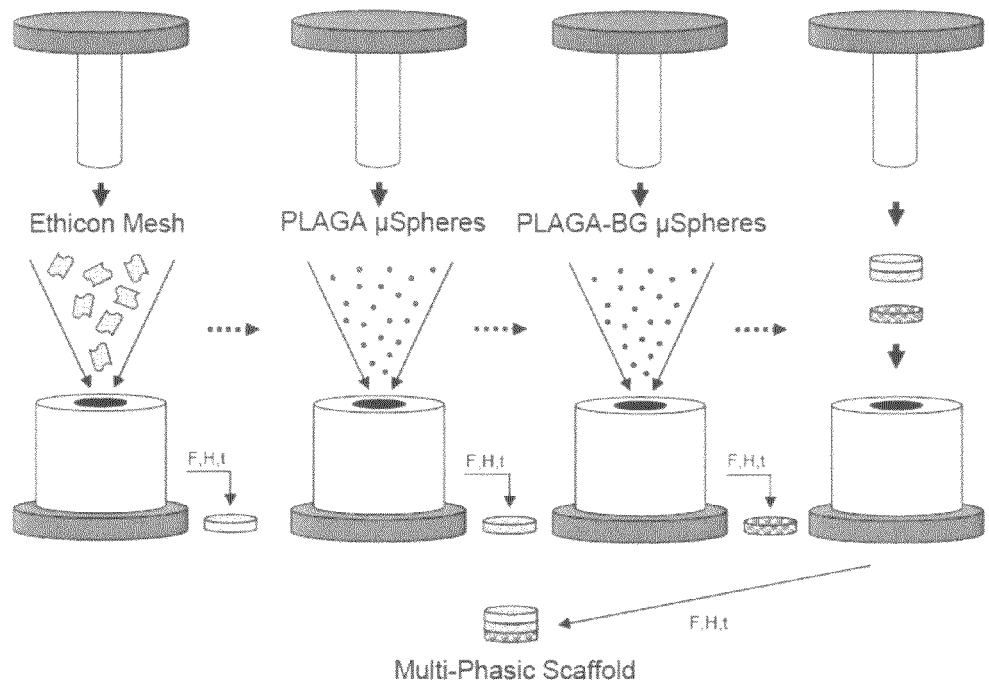
FIG. 32-1
FIG. 32-2
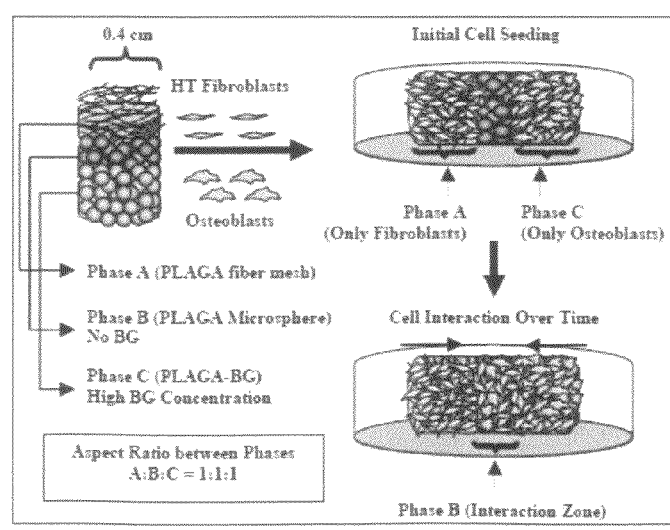

|  | Pore Area (mm2) | Intrusion Volume (μL) | Porosity (%) | Mode Pore Diam. (μm) |
|---|---|---|---|---|
| Phase A (n = 3) | 6000±800 | 41±8 | 58±5 | 73±11 |
| Phase B (n = 3) | 2400±500 | 28±7 | 34±4 | 75±7 |
| Phase C (n = 1) | 706.3 | 12.5 | 25.7 | 83 |

FIG. 32-5A
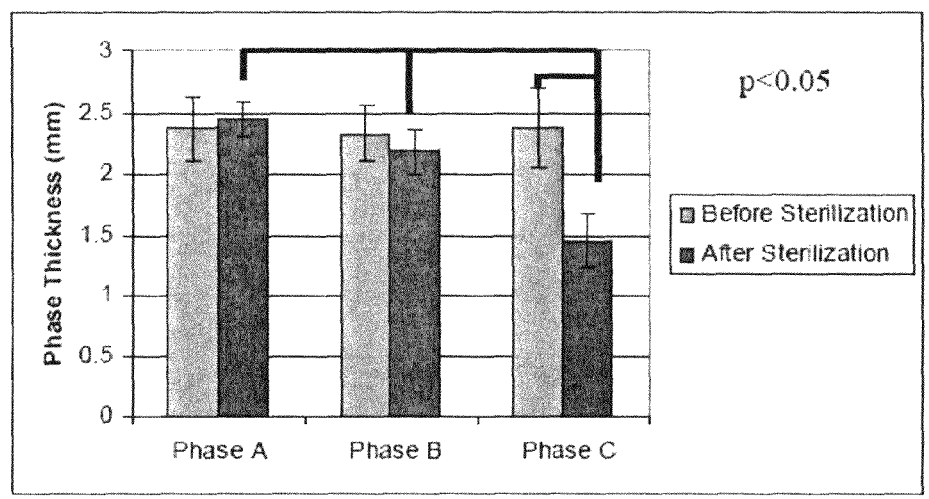
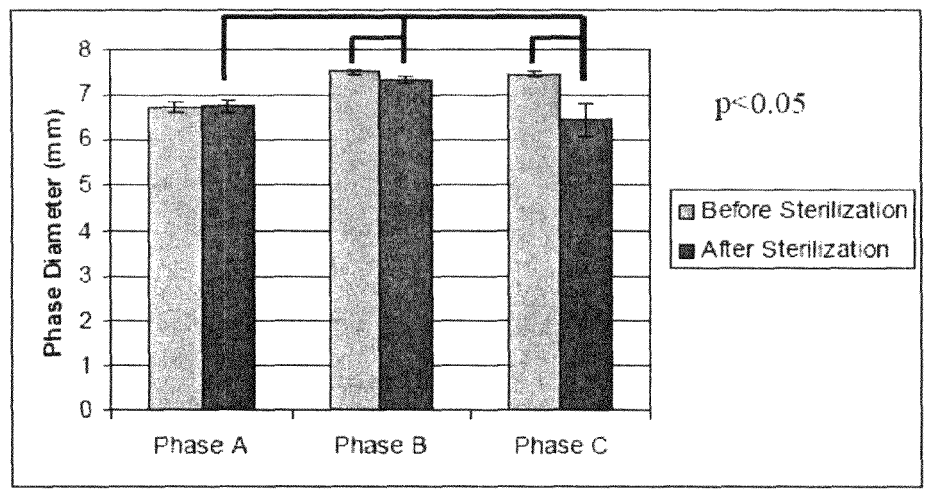
FIG. 32-5B

FIG. 32-6A
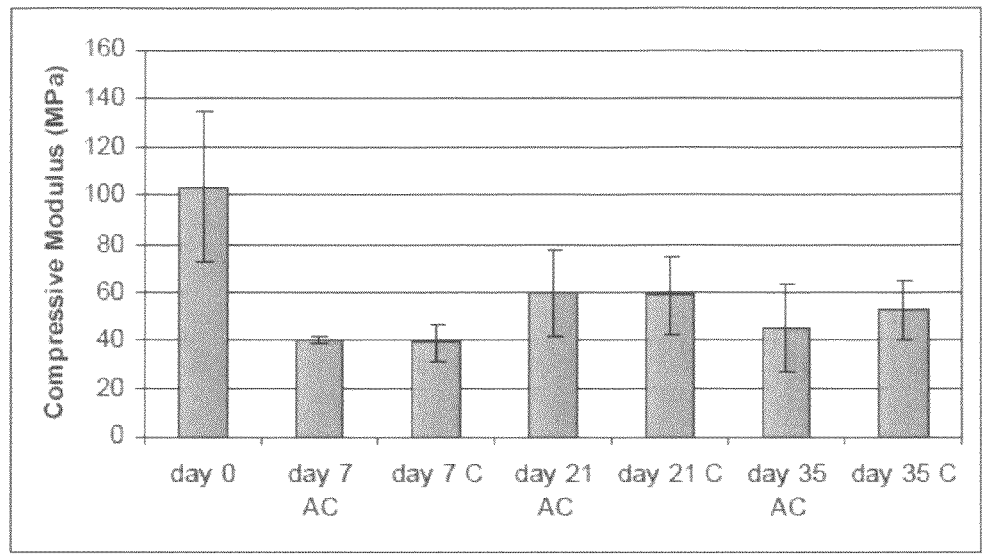
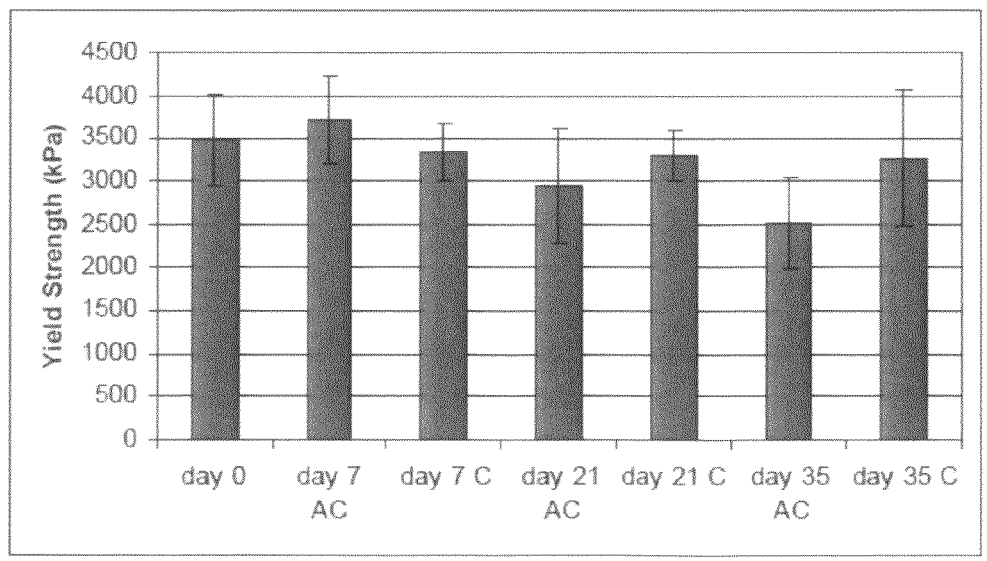
FIG. 32-6B

|   | PLAGA | DMF | EtOH |
|---|-------|-----|------|
| 1 | 20%   | 70% | 10%  |
| 2 | 30%   | 60% | 10%  |
| 3 | 40%   | 50% | 10%  |

| Gear | RPM  | Vs (m/s) |
|------|------|----------|
| 1st  | 23.2 | 7.4      |
| 2nd  | 29.5 | 9.4      |
| 3rd  | 46.2 | 15       |
| 4th  | 63.4 | 20       |

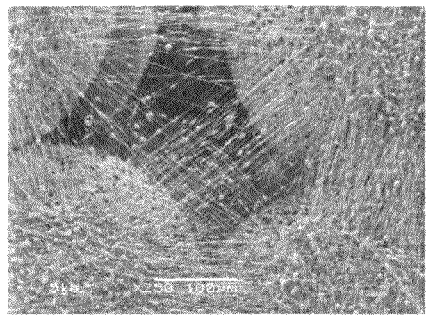 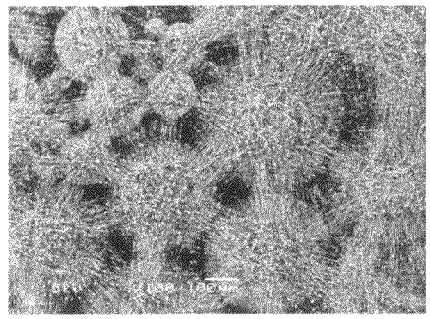
FIG. 33-4A  FIG. 33-4B
FIG. 34
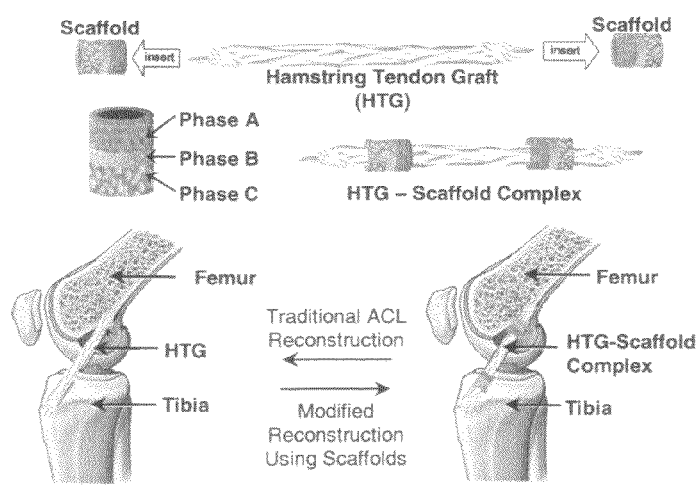

MULTI-PHASED, BIODEGRADABLE AND OSTEOINTEGRATIVE COMPOSITE SCAFFOLD FOR BIOLOGICAL FIXATION OF MUSCULOSKELETAL SOFT TISSUE OF BONE

CROSS-REFERENCE TO RELATED APPLICATIONS

This application is a continuation of U.S. Ser. No. 11/073,275, filed Mar. 4, 2005 now U.S. Pat. No. 7,767,221, which claims the benefit of U.S. Provisional Application No. 60/550,700, filed Mar. 5, 2004, the entire contents of each are hereby incorporated by reference herein.

BACKGROUND

Throughout this application, certain publications are referenced. Full citations for these publications, as well as additional related references, may be found immediately preceding the claims. The disclosures of these publications are hereby incorporated by reference into this application in order to more fully describe the state of the art as of the date of the methods and apparatuses described and claimed herein.

This application relates to musculoskeletal tissue engineering. For example, a scaffold apparatus is discussed below which can serve as a functional interface between multiple tissue types. Methods for preparing a multi-phase scaffold are also discussed. Some exemplary embodiments which include a soft tissue-bone interface are discussed.

As an example of a soft tissue-bone interface, the human anterior cruciate ligament (ACL) is described below. The ACL and ACL-bone interface are used in the following discussion as an example and to aid in understanding the description of the methods and apparatuses of this application. This discussion, however, is not intended to, and should not be construed to, limit the claims of this application.

The ACL consists of a band of regularly oriented, dense connective tissue that spans the junction between the femur and tibia. It participates in knee motion control and acts as a joint stabilizer, serving as the primary restraint to anterior tibial translation. The natural ACL-bone interface consists of three regions: ligament, fibrocartilage (non-mineralized and mineralized) and bone. The natural ligament to bone interface is arranged linearly from ligament to fibrocartilage and to bone. The transition results in varying cellular, chemical, and mechanical properties across the interface, and acts to minimize stress concentrations from soft tissue to bone.

The ACL is the most often injured ligament of the knee. Due to its inherently poor healing potential and limited vascularization, ACL ruptures do not heal effectively upon injury, and surgical intervention is typically needed to restore normal function to the knee.

Clinically, autogenous grafts based on either bone-patellar tendon-bone (BPTB) or hamstring-tendon (HST) grafts are often a preferred grafting system for ACL reconstruction, primarily due to a lack of alternative grafting solutions. Current ACL grafts are limited by donor site morbidity, tendonitis and arthritis. Synthetic grafts may exhibit good short term results but encounter clinical failure in long-term follow-ups, since they are unable to duplicate the mechanical strength and structural properties of human ACL tissue. ACL tears and ruptures are currently commonly repaired using semitendinosus grafts. Although semitendinosus autografts are superior, they often fail at the insertion site between the graft and the bone tunnel. One of the major causes of failure in this type of reconstruction grafts is its inability to regenerate the soft-tissue to bone interface.

Despite their distinct advantages over synthetic substitutes, autogenous grafts have a relatively high failure rate. A primary cause for the high failure rate is the lack of consistent graft integration with the subchondral bone within bone tunnels. The site of graft contact in femoral or tibial tunnels represents the weakest point mechanically in the early post-operative healing period. Therefore, success of ACL reconstructive surgery depends heavily on the extent of graft integration with bone.

ACL reconstruction based on autografts often results in loss of functional strength from an initial implantation time, followed by a gradual increase in strength that does not typically reach the original magnitude. Despite its clinical success, long term performance of autogenous ligament substitutes is dependent on a variety of factors, including structural and material properties of the graft, initial graft tension, intrarticular position of the graft, as well as fixation of the graft. These grafts typically do not achieve normal restoration of ACL morphology and knee stability.

There is often a lack of graft integration with host tissue, in particular at bony tunnels, which contributes to suboptimal clinical outcome of these grafts. The fixation sites at the tibial and femoral tunnels, instead of the isolated strength of the graft material, have been identified as mechanically weak points in the reconstructed ACL. Poor graft integration may lead to enlargement of the bone tunnels, and in turn may compromise the long term stability of the graft.

Increased emphasis has been placed on graft fixation, as post surgery rehabilitation protocols require the immediate ability to exercise full range of motion, reestablish neuromuscular function and weight bearing. During ACL reconstruction, the bone-patellar tendon-bone or hamstring-tendon graft is fixed into the tibial and femoral tunnels using a variety of fixation techniques. Fixation devices include, for example, staples, screw and washer, press fit EndoButton® devices, and interference screws. In many instances, EndoButton® devices or Mitek®Anchor devices are utilized for fixation of femoral insertions. Staples, interference screws, or interference screws combined with washers can be used to fix the graft to the tibial region.

Recently, interference screws have emerged as a standard device for graft fixation. The interference screw, about 9 mm in diameter and at least 20 mm in length, is used routinely to secure tendon to bone and bone to bone in ligament reconstruction. Surgically, the knee is flexed and the screw is inserted from the para-patellar incision into the tibial socket, and the tibial screw is inserted just underneath the joint surface. After tension is applied to the femoral graft and the knee is fully flexed, the femoral tunnel screw is inserted. This procedure has been reported to result in stiffness and fixation strength levels which are adequate for daily activities and progressive rehabilitation programs.

While the use of interference screws have improved the fixation of ACL grafts, mechanical considerations and bio-material-related issues associated with existing screw systems have limited the long term functionality of the ligament substitutes. Screw-related laceration of either the ligament substitute or bone plug suture has been reported. In some cases, tibial screw removal was necessary to reduce the pain suffered by the patient. Stress relaxation, distortion of magnetic resonance imaging, and corrosion of metallic screws have provided motivation for development of biodegradable screws based on poly-α-hydroxy acids. While lower incidence of graft laceration was reported for biodegradable screws, the highest interference fixation strength of the grafts to bone is reported to be 475 N, which is significantly lower than the attachment strength of ACL to bone. When tendon-to-bone fixation with polylactic acid-based interference screws was examined in a sheep model, intraligamentous failure was reported by 6 weeks. In addition, fixation strength is dependent on quality of bone (mineral density) and bone compression.

Two insertion zones can be found in the ACL, one at the femoral end and another located at the tibial attachment site. The ACL can attach to mineralized tissue through insertion of collagen fibrils, and there exists a gradual transition from soft tissue to bone. The femoral attachment area in the human ACL was measured to be $113\pm27$ mm$^2$ and $136\pm33$ mm$^2$ for the tibia insertion. With the exception of the mode of collagen insertion into the subchondral bone, the transition from ACL to bone is histologically similar for the femoral and tibial insertion sites.

The insertion site is comprised of four different zones: ligament, non-mineralized fibrocartilage, mineralized fibrocartilage, and bone. The first zone, which is the ligament proper, is composed of solitary, spindle-shaped fibroblasts aligned in rows, and embedded in parallel collagen fibril bundles of 70-150 µm in diameter. Primarily type I collagen makes up the extracellular matrix, and type III collagen, which are small reticular fibers, are located between the collagen I fibril bundles. The second zone, which is fibro-cartilaginous in nature, is composed of ovoid-shaped chondrocyte-like cells. The cells do not lie solitarily, but are aligned in rows of 3-15 cells per row. Collagen fibril bundles are not strictly parallel and much larger than those found in zone 1. Type II collagen is now found within the pericellular matrix of the chondrocytes, with the matrix still made up predominantly of type I collagen. This zone is primarily avascular, and the primary sulfated proteoglycan is aggrecan. The next zone is mineralized fibrocartilage. In this zone, chondrocytes appear more circular and hypertrophic, surrounded by larger pericellular matrix distal from the ACL. Type X collagen, a specific marker for hypertrophic chondrocytes and subsequent mineralization, is detected and found only within this zone. The interface between mineralized fibrocartilage and subjacent bone is characterized by deep inter-digitations. Increasing number of deep inter-digitations is positively correlated to increased resistance to shear and tensile forces during development of rabbit ligament insertions. The last zone is the subchondral bone and the cells present are osteoblasts, osteocytes and osteoclasts. The predominant collagen is type I and fibrocartilage-specific markers such as type II collagen are no longer present.

For bone-patellar tendon-bone grafts, bone-to-bone integration with the aid of interference screws is the primary mechanism facilitating graft fixation. Several groups have examined the process of tendon-to-bone healing.

Blickenstaff et al. (1997) evaluated the histological and biomechanical changes during the healing of a semitendinosus autograft for ACL reconstruction in a rabbit model. Graft integration occurred by the formation of an indirect tendon insertion to bone at 26 weeks. However, large differences in graft strength and stiffness remained between the normal semi-tendinosus tendon and anterior cruciate ligament after 52 weeks of implantation.

In a similar model, Grana et al. (1994) reported that graft integration within the bone tunnel occurs by an intertwining of graft and connective tissue and anchoring of connective tissue to bone by collagenous fibers and bone formation in the tunnels. The collagenous fibers have the appearance of Sharpey's fibers seen in an indirect tendon insertion.

Rodeo et al. (1993) examined tendon-to-bone healing in a canine model by transplanting digital extensor tendon into a bone tunnel within the proximal tibial metaphysis. A layer of cellular, fibrous tissue was found between the tendon and bone, and this fibrous layer matured and reorganized during the healing process. As the tendon integrated with bone through Sharpey's fibers, the strength of the interface increased between the second and the twelfth week after surgery. The progressive increase in strength was correlated with the degree of bone in growth, mineralization, and maturation of the healing tissue.

In most cases, tendon-to-bone healing with and without interference fixation does not result in the complete re-establishment of the normal transition, zones of the native ACL-bone insertions. This inability to fully reproduce these structurally and functionally different regions at the junction between graft and bone is detrimental to the ability of the graft to transmit mechanical stress across the graft proper and leads to sites of stress concentration at the junction between soft tissue and bone.

Zonal variations from soft to hard tissue at the interface facilitate a gradual change in stiffness and can prevent build up of stress concentrations at the attachment sites.

The insertion zone is dominated by non-mineralized and mineralized fibrocartilage, which are tissues adept at transmitting compressive loads. Mechanical factors may be responsible for the development and maintenance of the fibrocartilagenous zone found at many of the interfaces between soft tissue and bone. The fibrocartilage zone with its expected gradual increase in stiffness appears less prone to failure.

Benjamin et al. (1991) suggested that the amount of calcified tissue in the insertion may be positively correlated to the force transmitted across the calcified zone.

Using simple histomorphometry techniques, Gao et al. determined that the thickness of the calcified fibrocartilage zone was $0.22\pm0.7$ mm and that this was not statistically different from the tibial insertion zone. While the ligament proper is primarily subjected to tensile and torsional loads, the load profile and stress distribution at the insertion zone is more complex.

Matyas et al. (1995) combined histomorphometry with a finite element model (FEM) to correlate tissue phenotype with stress state at the medial collateral ligament (MCL) femoral insertion zone. The FEM model predicted that when the MCL is under tension, the MCL midsubstance is subjected to tension and the highest principal compressive stress is found at the interface between ligament and bone.

Calcium phosphates have been shown to modulate cell morphology, proliferation and differentiation. Calcium ions can serve as a substrate for $Ca^{2+}$-binding proteins, and modulate the function of cytoskeleton proteins involved in cell shape maintenance.

Gregiore et al. (1987) examined human gingival fibroblasts and osteoblasts and reported that these cells underwent changes in morphology, cellular activity, and proliferation as a function of hydroxyapatite particle sizes. Culture distribution varied from a homogenous confluent monolayer to dense, asymmetric, and multi-layers as particle size varied from less than 5 µm to greater than 50 µm, and proliferation changes correlated with hydroxyapatite particles size.

Cheung et al. (1985) further observed that fibroblast mitosis is stimulated with various types of calcium-containing complexes in a concentration-dependent fashion.

Chondrocytes are also dependent on both calcium and phosphates for their function and matrix mineralization. Wuthier et al. (1993) reported that matrix vesicles in fibrocartilage consist of calcium-acidic phospholipids-phosphate complex, which are formed from actively acquired calcium ions and an elevated cytosolic phosphate concentration.

Phosphate ions have been reported to enhance matrix mineralization without regulation of protein production or cell proliferation, likely because phosphate concentration is often the limiting step in mineralization. It has been demonstrated that human foreskin fibroblasts when grown in micromass cultures and under the stimulation of lactic acid can dedifferentiate into chondrocytes and produce type II collagen.

Cheung et al. (1985) found a direct relationship between β-glycerophosphate concentrations and mineralization by both osteoblasts and fibroblasts. Increased mineralization by ligament fibroblasts is observed with increasing concentration of β-glycerophosphate, a media additive commonly used in osteoblast cultures. These reports strongly suggest the plasticity of the fibroblast response and that the de-differentiation of ligament fibroblasts is a function of mineral content in vitro.

Progressing through the four different zones which make up the native ACL insertion zone, several cell types are identified: ligament fibroblasts, chondrocytes, hypertrophic chondrocytes and osteoblasts, osteoclasts, and osteocytes. The development of in vitro multi-cell type culture systems facilitates the formation of the transition zones.

No reported studies on either the co-culture of ligament fibroblasts with osteoblasts, nor on the in vitro and in vivo regeneration of the bone-ligament interface are known.

No reported studies which examine the potential of multi-phased scaffolds in facilitating the fixation of ligament or tendon to bone are known. As the interface between graft and bone is the weakest point during the initial healing period, recent research efforts in ACL tissue engineering have concentrated on design of multi-phased scaffolds in order to promote graft integration.

Goulet et al. (2000) developed a bio-engineered ligament model, where ACL fibroblasts were added to the structure and bone plugs were used to anchor the bioengineered tissue. Fibroblasts isolated from human ACL were grown on bovine type I collagen, and the bony plugs were used to promote the anchoring of the implant within the bone tunnels.

Cooper et al. (2000) and Lu et al. (2001) developed a tissue engineered ACL scaffold using biodegradable polymer fibers braided into a 3-D scaffold. This scaffold has been shown to promote the attachment and growth of rabbit ACL cells in vitro and in vivo. However, no multiphased scaffolds for human ligament-to-bone interface are known.)

SUMMARY

This application describes scaffold apparatuses for musculoskeletal tissue engineering.

A scaffold apparatus, according to one preferred embodiment, is multi-phasic and can support growth, maintenance and differentiation of multiple tissue and cell types. The multi-phasic scaffold apparatus has a gradient of calcium phosphate content across the phases, and is biomimetic, biodegradable and/or osteointegrative.

A scaffold apparatus, according to another embodiment, includes microspheres of selected sizes and/or composition. The microspheres are layered to have a gradient of microsphere sizes and/or compositions. The scaffold provides a functional interface between multiple tissue types.

A multi-phased scaffold apparatus for providing a functional interface between bone and soft tissue is also described. The multi-phased scaffold apparatus, according to one embodiment, includes microspheres as one phase of the scaffold, and a mesh as another phase of the scaffold. The microspheres and the mesh are sintered together.

A scaffold apparatus for soft tissue-to-bone interface tissue engineering is also described. The apparatus comprises four (or more) regions. The first region comprises composite microspheres of a first size and composition optimized to promote growth, proliferation, and differentiation of a first cell type for integration and growth of a first tissue type. The second region is joined to the first region, and comprises microspheres and/or a fibrous mesh which have a second size and a second composition. The third region is joined to the second region, and comprises microspheres and/or a fibrous mesh which has a third size and a third composition. The second and third regions are optimized to promote growth, proliferation and differentiation of a second cell type for integration and formation of a second tissue type. The fourth region is joined to the third region, and comprises microspheres and/or a fibrous mesh which have a composition adapted to promote growth, proliferation, and differentiation of a third cell type for integration and growth of a third tissue type.

This application also describes methods for preparing a scaffold for musculoskeletal tissue engineering. According to one exemplary embodiment, a method for preparing a scaffold comprises (a) processing a plurality of microspheres, including incorporating calcium phosphate (and/or bioglass) into the microspheres, (b) laying the processed microspheres in a mold, the microspheres in the mold presenting a gradient of microsphere sizes and/or compositions, and (c) sintering together the microspheres in the mold above the polymer glass transition temperature.

According to another embodiment, a method for preparing a multi-phase scaffold for musculoskeletal tissue engineering. The method, according to one embodiment, comprises (a) processing a plurality of microspheres, including incorporating calcium phosphate (and/or bioglass) into the microspheres, (b) laying the processed microspheres in a mold, wherein the microspheres in the mold present a gradient of microsphere sizes for a first phase and a second phase of the multi-phase scaffold, with microspheres of the first phase being in a first range of sizes, and with microspheres of the second phase being in a second range of sizes larger than the first range of sizes, (c) sintering together the microspheres in the mold above a glass transition temperature, and (d) sintering a fiber mesh, as a third phase of the multi-phase scaffold, onto the microsphere construct prepared in (c).

According to another exemplary embodiment, a method for preparing a multi-phase scaffold for musculoskeletal tissue engineering, can comprise the steps of (a) forming a mesh scaffold by sintering together a plurality of mesh segments as a first phase of the multi-phase scaffold, (b) forming a second scaffold by sintering together a plurality of poly-lactide-co-glycolide microspheres as a second phase of the multi-phase scaffold, (c) forming a third scaffold by sintering together a plurality of microspheres formed of a composite of poly-lactide-co-glycolide and bioactive glass as a third phase of the multi-phase scaffold, and (d) sintering together said mesh scaffold, said second scaffold and said third scaffold.

This application also describes methods for producing polymer/ceramic composite microspheres.

BRIEF DESCRIPTION OF THE FIGURES

The patent or application file contains at least one drawing executed in color. Copies of this patent or patent application publication with color drawing(s) will be provided by the Office upon request and a payment of the necessary fee.

FIG. 1A shows a schematic diagram of a scaffold apparatus, according to one embodiment.

FIG. 1B shows a schematic diagram of a scaffold apparatus, according to another embodiment FIG. 2 shows a schematic diagram of a multi-phased scaffold apparatus, according to another embodiment.

FIG. 3 shows a flow chart for a method for preparing a scaffold, according to an exemplary embodiment.

FIG. 4A shows a flow chart for a method for preparing a multi-phased scaffold, according to another embodiment. FIG. 4B shows a flow chart for a method for preparing a scaffold, according to another exemplary embodiment.

FIG. 8B: 500X).

FIG. 11B shows the formation of Ca—P over time.

FIG. 14 shows higher type I collagen type synthesis on PLAGA-BG.

FIG. 15A: ALZ stain, ACL fibroblasts 14 days, 20×;
FIG. 15B: ALZ stain, interface, ACL 14 days, 20×;
FIG. 15C: ALZ stain, osteoblasts, ACL 14 days, 20×.
FIG. 16A: ALP stain, ACL fibroblasts, 7 days, 32×;
FIG. 16B: ALP+DAPI stain, co-culture, 7 days, 32×;
FIG. 16C: ALP stain, osteoblasts, 7 days, 32×.

FIGS. 17A-17F show images of multiphase scaffold (FIGS. 17A-17C) and blow-ups of respective sections (FIGS. 17D-17F).

FIGS. 18A-18C show multiphasic scaffold for co-culture of ligament fibroblasts and osteoblasts; FIG. 18A and FIG. 18B: images of a sample scaffold; FIG. 18C: schematic of scaffold design depicting the three layers.

FIGS. 19A-19D show Micromass co-culture samples after 14 days. FIG. 19A: H&E stain; FIG. 19B: Alcian blue; FIG. 19C: Type I collagen (green); FIG. 19D: Type II collagen (green)+Nucleic stain (red).

FIGS. 20A and 20B show RT-PCR gel for day 7 micromass samples. FIG. 20A: Type X collagen expression. FIG. 20B: Type II collagen expression. (C: control micromass sample; E: experimental co-culture sample).

FIGS. 21A and 21B show SEM image of cellular attachment to PLAGA-BG scaffold after 30 min; FIG. 21A: chondrocyte control (2000X); FIG. 21B: co-culture (1500X).

FIGS. 22A-22C show Cellular attachment to PLAGA-BG scaffold; FIG. 22A: chondrocyte control, day 1 (500X); FIG. 22B: co-culture, day 1 (500X). FIG. 22C: co-culture, day 7 (750X).

FIG. 23 shows a tabular summary of results from structural characterizations of an as-fabricated composite scaffold.

FIG. 28-1 shows a table of porosimetry data, including intrusion volume, porosity, and pore diameter data, in another set of experiments.

FIGS. 28-2A through 28-2C show fluorescence microscopy images (day 28, ×10) for Phases A through C, respectively.

FIGS. 28-3A and 28-3B are images showing extracellular matrix production for Phases B and C, respectively.

FIGS. 29-1A through 29-1D show SEM images, in another set of experiments:
  A) Phase C, Day 0-×1000;
  B) Phase C, Day 28-×1000;
  C) Phase A, Day 28-×1000; and
  D) Phase B, Day 28-×70.

FIGS. 29-2A through 29-2F show fluorescence microscopy images:
  A) Phase A, Day 0, ×10;
  B) Phase B, Day 0, ×10;
  C) Phase C, Day 0, ×10;
  D) Phase A, Day 28, ×10;
  E) Phase B, Day 28, ×10; and
  F) Phase C, Day 28, ×10.

FIGS. 29-3A1 through 29-3A3 show Trichrome images (Day 0, ×10) of Phase A, Phase B and Phase C, respectively.

FIGS. 29-3B1 and 29-3B2 show Picrosirius Red images of Phase B and Phase C, respectively.

FIGS. 29-3C shows a von Kossa image of Phase C.

FIGS. 30-1a through 30-1f show images of osteoblast and fibroblast in culture, in another set of experiments:
  a) Day 0, 5×;
  b) Day 0, 5×;
  c) Day 1, 5×;
  d) Day 2, 5×;
  e) Day 1, 32× (cell contact); and
  f) Day 1, 32×.

FIGS. 30-2a through 30-2c show stained images:
  a) live-dead stain of 1 hr sample, 5×;
  b) ALP stain of ob and fb, day 2, 20×; and
  c) collagen I staining, day 6, 20×.

FIG. 31-1 shows a schematic of the experimental design, in another set of experiments, for in vitro evaluations of human osteoblasts and fibroblasts co-cultured on multi-phased scaffolds.

FIG. 31-2 shows a graph which demonstrates cell proliferation in Phases A, B, and C during 35 days of human hamstring tendon fibroblast and osteoblast co-culture on multiphased scaffolds.

FIGS. 31-3A and 31-3B graphically show Mechanical testing data for multiphased scaffolds seeded with human hamstring tendon fibroblasts and human osteoblasts over 35 days of culture (n=4).

FIG. 32-1 schematically shows a method for producing multi-phasic scaffolds, in another set of experiments. First, Ethicon PLAGA mesh is cut into small pieces and inserted into a mold. By applying compression force (F) and heating (H) at 150° C. for time (t)=20 hours, the mesh segments are sintered into a mesh scaffold, which is removed from the mold. Next, PLAGA microspheres are inserted into the mold, sintered, then removed as a second scaffold. The same process is performed for the PLAGA-BG microspheres. Finally, Phases A and B are joined by solvent evaporation, then all three scaffolds are inserted into the mold and sintered together, forming the final multi-phasic scaffold.

FIG. 32-2 shows a schematic of a co-culture experimental design.

FIG. 32-3 shows a table summarizing mercury porosimetry data.

FIGS. 32-5A and 32-5B show graphically scaffold phase thicknesses and diameters, in the experiments of FIG. 32-1 through FIG. 32-3.

FIG. 32-4 shows graphically a comparison of microsphere initial mass and final mass after undergoing a sintering process.

FIGS. 32-6A and 32-6B show graphically mechanical testing data for multiphased scaffolds seeded with human hamstring tendon fibroblasts and human osteoblasts over days of culture (n=4). Scaffolds were tested in uniaxial compression. Compressive modulus (A) and yield strength (B) were calculated from the resulting stress-strain curves. Both cell seeded (C) and acellular (AC) scaffolds were examined at days 0, 7, 21, and 35. Scaffold compressive modulus was significantly greater at day 0 than for all subsequent time points and groups ($p<0.05$).

FIG. 33-1 shows a table illustrating the compositions of polymer solutions tested, in another set of experiments.

FIG. 33-2 shows a table illustrating drum rotational velocity (rpm) and surface velocity (m/s) for each gear.

FIGS. 33-3A and 33-3D show SEMS of electrospun meshes spun at:
A) $1^{st}$ gear, 7.4 m/s;
B) $2^{nd}$ gear, 9.4 m/s;
C) $3^{rd}$ gear, 15 m/s; and
D) $4^{th}$ gear, 20 m/s.

FIGS. 33-4A and 33-4B show scanning electron microscopy (SEM) images of another embodiment of multi-phased scaffold, with 85:15 PLAGA electrospun mesh joined with PLAGA:BG composite microspheres.

FIG. 34 schematically shows one exemplary embodiment of multi-phased scaffold as a hamstring tendon graft collar which can be implemented during ACL reconstruction surgery to assist with hamstring tendon-to-bone healing.

DETAILED DESCRIPTION

Figures 5A, 5B, 5C:
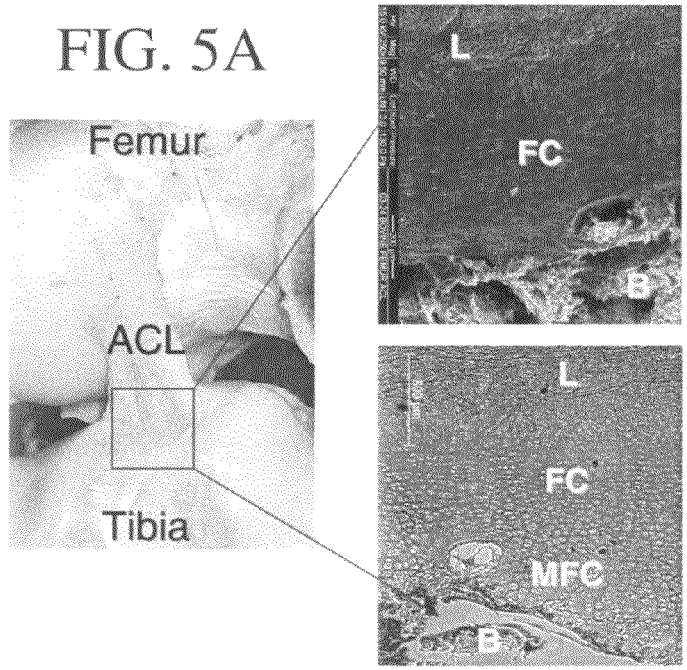
FIG. 5A: Posterior view of an intact bovine anterior cruciate ligament (ACL) connecting the femur to the tibia (left).
FIG. 5B: Environmental scanning electron microscope (ESEM) image of transition from ligament (L) to fibrocartilage (FC) to bone (B) at the ACL insertion (upper right).
FIG. 5C: Histological micrograph of similar ACL to bone interface additionally showing mineralized fibrocartilage (MFC) zone (lower right).

In order to facilitate an understanding of the material which follows, one may refer to Freshney, R. Ian. *Culture of Animal Cells—A Manual of Basic Technique* (New York: Wiley-Liss, 2000) for certain frequently occurring methodologies and/or terms which are described therein.

However, except as otherwise expressly provided herein, each of the following terms, as used in this application, shall have the meaning set forth below.

As used herein, "bioactive" shall include a quality of a material such that the material has an osteointegrative potential, or in other words the ability to bond with bone. Generally, materials that are bioactive develop an adherent interface with tissues that resist substantial mechanical forces.

As used herein, "biomimetic" shall mean a resemblance of a synthesized material to a substance that occurs naturally in a human body and which is not rejected by (e.g., does not cause an adverse reaction in) the human body.

As used herein, "chondrocyte" shall mean a differentiated cell responsible for secretion of extracellular matrix of cartilage.

As used herein, "fibroblast" shall mean a cell of connective tissue, mesodermally derived, that secretes proteins and molecular collagen including fibrillar procollagen, fibronectin and collagenase, from which an extracellular fibrillar matrix of connective tissue may be formed.

Generally, "glass transition temperature" is the temperature at which, upon cooling, a noncrystalline ceramic or polymer transforms from a supercooled liquid into a rigid glass. The noncrystalline ceramic or polymer may be of multiple form and composition, and may be formed as microspheres. In the context of a sintering process, such as discussed in this application, the polymer chains from adjacent microspheres typically entangle, effectively forming a bond between the microspheres upon cooling. As the polymer is heated above its glass transition temperature, long range polymer chain motion begins.

As used herein, "graft fixation device" shall mean a device for fixation of a graft, including but not limited to staples, interference screws with or without washers, press fit EndoButton® devices and Mitek® Anchor devices.

As used herein, "interference screw" shall mean a device indicated for soft tissue-bone fixation. The device may be used in, for example, anterior cruciate ligament surgery. The device may include, but is not limited to, at least titanium cannulated interference screws, PLLA absorbable interference screws, and Poly-L-Lactide interference screws.

As used herein, "matrix" shall mean a three-dimensional structure fabricated from biomaterials. The biomaterials can be biologically-derived or synthetic.

As used herein, "osteoblast" shall mean a bone-forming cell that is derived from mesenchymal osteoprognitor cells and forms an osseous matrix in which it becomes enclosed as an osteocyte. The term is also used broadly to encompass osteoblast-like, and related, cells, such as osteocytes and osteoclasts.

As used herein, "osteointegrative" shall mean ability to chemically bond to bone.

As used herein, "polymer" shall mean a chemical compound or mixture of compounds formed by polymerization and including repeating structural units. Polymers may be constructed in multiple forms and compositions or combinations of compositions.

As used herein, "porosity" shall mean the ratio of the volume of interstices of a material to a volume of a mass of the material.

As used herein, "particle reinforcement" shall mean a process for forming a composite with a higher strength than the original material (for example, a polymer) by adding particles of a reinforcing material with a higher strength (for example, a ceramic).

As used herein, "sintering" shall mean densification of a particulate polymer compact involving a removal of pores between particles (which may be accompanied by equivalent shrinkage) combined with coalescence and strong bonding between adjacent particles. The particles may include particles of varying size and composition, or a combination of sizes and compositions.

This application describes scaffolds having a gradient of properties (such as structural properties, pore diameter, chemical properties, mechanical properties, etc.), for the repair of musculoskeletal tissue. The scaffold is preferably multi-phased, biodegradable, and osteointegrative.

The following exemplary embodiments and experimental details sections are set forth to aid in an understanding of the subject matter of this disclosure but are not intended to, and should not be construed to, limit in any way the invention as set forth in the claims which follow thereafter.

A scaffold apparatus, according to one preferred embodiment, is multi-phasic, including first, second and third phases, and preferably can support growth, maintenance and differentiation of multiple tissue and cell types.

The first phase comprises a first material adapted for integration and growth (for example, by including one or more osteogenic agents, osteogenic materials, osteoinductive agents, osteoinductive materials, osteoconductive agents, osteoconductive materials, growth factors, chemical factors, etc.) of a first tissue type and is seeded with a first type of cells (for example, osteoblasts, osteoblast-like cells, stem cells, etc.). The material of the first phase may include, but is not limited to, microspheres, foams, sponges and any other three dimensional (3-D) scaffold construct consisting of polymer and/or ceramic. Polymers may include, but is not restricted to, any biodegradable polymer such as any of the poly-(α-hydroxy acids), or natural polymers such as silk, collagen, or chitosan. Ceramics may include but are not limited to bioactive glass, hydroxyapatite, beta tricalcium phosphate, or any other calcium phosphate material.

The third phase comprises a second material adapted for integration and growth of a second tissue type seeded with a second type of cells (for example, fibroblasts, chondrocytes, stem cells, etc.). The third phase may include a composite of materials, including, but not limited to, microspheres, a fiber mesh, degradable polymers, etc.

The second phase is an interfacial zone between the first and third phases.

The multi-phasic scaffold apparatus preferably has a gradient of calcium phosphate content across the phases, and is preferably biomimetic, biodegradable (that is, each phase is degradable) and/or osteointegrative.

A scaffold apparatus for musculoskeletal tissue engineering, according to another embodiment, may include microspheres of selected sizes and/or composition. The microspheres may be layered to have a gradient of microsphere sizes and/or compositions. The scaffold may provide a functional interface between multiple tissue types (for example, soft tissue and bone).

FIG. 1A shows schematically a multi-phased scaffold apparatus 10 comprising phase A, phase B, and phase C. Phases A-C have a gradient of properties. The gradient of properties across phases A-C of the scaffold may include mineral content (for example, Ca—P), mechanical properties, chemical properties, structural properties, porosity, geometry, etc. It should be apparent to one skilled in the art that although apparatus 10 has three phases, the apparatus can be integrated in a scaffold with four or more phases.

For example, the multi-phased scaffold may contain a gradient of Ca—P concentrations. Phase A may be constructed of fiber mesh with aligned fibers and with no Ca—P, phase C may be constructed of polymer-ceramic composite with high Ca—P, and phase B may be constructed of polymer-ceramic composite with lower Ca—P than phase C.

The scaffold apparatus can promote growth and maintenance of multiple tissue types. The scaffold may support growth, maintenance and differentiation of multiple tissue and cell types. The multi-phased scaffold may mimic the inhomogeneous properties of the insertion zone between soft tissue and bone, resulting in desired growth, phenotypic expression, and interactions between relevant cell types.

The phases of the scaffold may be inhomogeneous in properties. The phases may have zonal differences in mineral content and matrix morphology designed to mimic the tissue-bone interface and to facilitate the growth and maintenance of different tissues. The phases may differ in morphology. For example, phase A can include a porous fibrous mesh, while phases B and C include microspheres. According to another embodiment, the scaffold may include a composite of microspheres and a fiber mesh.

The scaffold preferably includes multiple phases. According to one embodiment, one phase (for example, phase A) supports growth and maintenance of soft tissue, another phase (for example, phase C) supports growth and maintenance of bone, and a third phase is an interfacial zone between the first and second phases. The first phase for supporting growth and maintenance of the soft tissue may be seeded with at least one of fibroblasts, chondrocytes and stem cells. The second phase for supporting growth and maintenance of the bone may be seeded with at least one of osteoblasts, osteoblast-like cells and stem cells. The second phase can contain at least one of osteogenic agents, osteogenic materials, osteoinductive agents, osteoinductive materials, osteoconductive agents, osteoconductive materials, growth factors and chemical factors.

Further, at least one of said first phase and said second phase may be seeded with one or more agents by using a microfluidic system.

The third phase may include some of the microspheres. The third phase can include a gradient of microsphere sizes and/or a gradient of microsphere compositions. The microspheres in the third phase may be joined by sintering in at least one stage.

The second phase may include additional microspheres. The second phase can comprise one of polymeric and composite microspheres including a range of diameters or a gradient of diameter. At least some of the microspheres of the third phase may be in a first range of sizes, and the additional microspheres of the second phase may be in a second range of sizes lower than the first range of sizes.

The second phase can comprise polymeric hydrogels of one of polyethylene glycol and hydroxyethyl methacrylate. The hydrogel may comprise one or more of poly(ethylene glycol), agarose, alginate, 2-hydroxyethyl methacrylate and polyacrylamide. The second phase can comprise collagen gels with varied mineral content.

The scaffold may include a composite of microspheres and a fiber mesh. The fiber mesh may be a degradable polymer. For example, the first phase may include a fiber mesh. The fiber mesh of the first phase and the microspheres of the third phase may be sintered together. The fiber mesh may be electrospun.

The mesh can include one or more desired agents and/or compound. For example, at least one of bioactive agents and peptides may coat the surface of the mesh. The bioactive agents and peptides can enhance differentiation, proliferation and attachment of cells and specific cell types. Also or alternatively, at least one of bioactive agents and peptides can directly be incorporated into the mesh.

According to one embodiment, the scaffold may include multiple phases joined by a gradient of properties. The multiple phases joined by the gradient of properties may be processed through one or more sintering stages. The gradient of properties across the multiple phases of the scaffold can include mechanical properties, chemical properties, mineral content, structural properties, porosity and/or geometry.

The scaffold apparatus can include plural phases of microspheres. For example, a first phase of the microspheres can comprise polymer and a second phase of the microspheres can comprise one of bioactive glass and calcium phosphate. Varying concentrations of calcium phosphate can be incorporated into the microspheres. The calcium phosphate can be selected from a group comprising tricalcium phosphate, hydroxyapatite, and a combination thereof. The polymer can be selected from a group comprising aliphatic polyesters, poly(amino acids), copoly(ether-esters), polyalkylenes oxalates, polyamides, poly(iminocarbonates), polyorthoesters, polyoxaesters, polyamidoesters, poly(ε-caprolactone)s, polyanhydrides, polyarylates, polyphosphazenes, polyhydroxyalkanoates, polysaccharides, and biopolymers, and a blend of two or more of the preceding polymers. The polymer can comprise at least one of poly(lactide-co-glycolide), poly(lactide) and poly(glycolide).

The microspheres may comprise one or more of CaP, bioactive glass, polymer, etc. The microspheres may be processed through one or more sintering stages.

The microspheres may comprise one or more desired agents or compounds. For example, at least one of bioactive agents and peptides may coat the surface of at least some of the microspheres. The bioactive agents and peptides can enhance at least one of differentiation, proliferation and attachment of cells and specific cell types. Also or alternatively, at least one of bioactive agents and peptides can directly be incorporated into at least some of the microspheres. The microspheres can additionally include one or more agents selected from a group comprising antiinfectives, hormones, analgesics, anti-inflammatory agents, growth factors, chemotherapeutic agents, anti-rejection agents and RGD peptides.

The apparatus is preferably biomimetic, biodegradable and/or osteointegrative.

According to one exemplary embodiment, the apparatus may be integrated in a graft fixation device. The graft fixation device may be used, for example, for graft fixation at the bone tunnels during anterior cruciate ligament reconstruction.

According to another embodiment, the apparatus may be integrated in an interference screw.

In addition, the scaffold apparatus, according to another exemplary embodiment, may be integrated in a graft collar. The graft collar has many applications. For example, the graft collar may be adapted for hamstring tendon-to-bone healing. As another example, the graft collar can be adapted for peridontal ligament repair. Further, the graft collar may be adapted for spinal repair.

A scaffold apparatus for soft tissue-to-bone interface tissue engineering, according to another exemplary embodiment, is shown schematically in FIG. 1B. Apparatus 15 includes a first region H, a second region I which is joined to region H, a third region J which is joined to region I, and a fourth region K which is joined to region J.

Region H comprises composite microspheres of a first size and composition optimized to promote growth, proliferation, and differentiation of a first cell type for integration and growth of a first tissue type. The composite microspheres of region H can include a range of sizes.

Region I comprises at least one of microspheres and a fibrous mesh having a second size and a second composition. The microspheres and/or fibrous mesh of region I can include a range or gradient of sizes, and/or a gradient of compositions.

Region J comprises at least one of a microsphere and a fibrous mesh having a third size and a third composition. Regions I and J are optimized to promote growth, proliferation and differentiation of a second cell type for integration and formation of a second tissue type. The microspheres and/or fibrous mesh of region J can include a range or gradient of sizes, and/or a gradient of compositions.

Region K comprises at least one of a microsphere and a fibrous mesh having a composition adapted to promote growth, proliferation, and differentiation of a third cell type for integration and growth of a third tissue type. The fibrous mesh may be electrospun.

The regions H-K can be joined together through one of a solid state sintering process and a solvent aggregation process, in which selected growth factors or bioactive agents are incorporated into each region to promote formation, growth and integration of said first, second and third types of tissues. The scaffold apparatus may be integrated in a graft collar.

Figures 1, 2, 30:
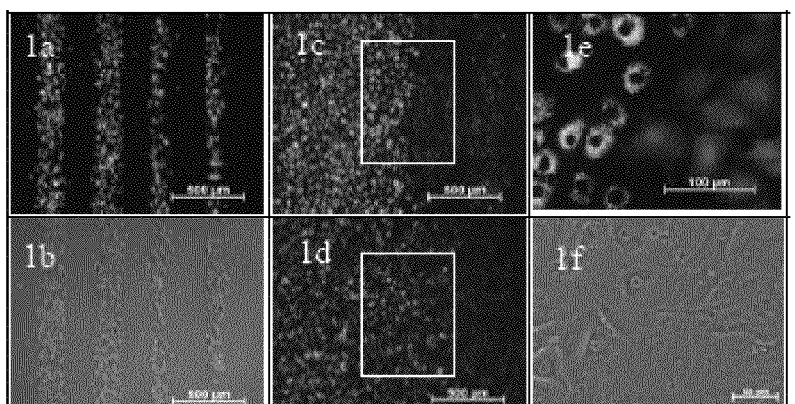

A multi-phased scaffold apparatus for providing a functional interface between bone and soft tissue, according to an embodiment schematically shown in FIG. 2, includes microspheres as one phase, and a mesh as another phase. The microspheres and the mesh may be sintered together.

FIG. 2 shows schematically a multi-phased scaffold apparatus 20 comprising phase X and phase Y. Microspheres may be one phase of the scaffold and a mesh may be another phase of the scaffold. The microspheres and the mesh may be sintered together. The apparatus 20 may be integrated in a scaffold which includes multiple phases (for example, three or more).

The microsphere and mesh structure of the scaffold may be geometrically heterogeneous, including a fiber mesh for culturing fibroblasts and an open-pore structure for osteoblasts. At least one zone of hydrogels or open-pore structure for chondrocytes may also be included. The microsphere and mesh components may be incorporated into the scaffold to allow for the co-culturing of multiple cell types to mimic the multitude of cell types found at native tissue interfaces. The mesh can be electrospun.

The scaffold may be modified to achieve specific cell culture parameters, for example, by including microspheres of varying diameters to vary the porosity of the scaffold in different regions. Furthermore, the scaffold may be fabricated in a variety of geometries. For example, the scaffold apparatus can be integrated in a graft collar.

This application also describes methods for preparing a scaffold for musculoskeletal tissue engineering. A method, according to one embodiment (FIG. 3), includes (a) processing a plurality of microspheres (step S31), including incorporating calcium phosphate into the microspheres, (b) laying the processed microspheres in a mold (step S33), the microspheres in the mold presenting a gradient of microsphere sizes and/or compositions, and (c) sintering together the microspheres in the mold above a glass transition temperature (step S35).

Additional steps may optionally be added to the method to impart additional scaffold features or characteristics. For example, the method may further include sintering a fiber mesh onto the microsphere construct to provide a functional interface between multiple tissue types. Further, the method may further comprise electrospinning said fiber mesh prior to attaching the electrospun fiber mesh onto the microsphere construct.

Varying concentrations of calcium phosphate may be incorporated into the microspheres. The calcium phosphate incorporated into the microspheres may include hydroxyapatite, tricalcium phosphate, etc.

The particulate phase of the microspheres may include bioactive glass. Varying porosity or concentrations of bioactive glass may be incorporated into the microspheres.

The method may further include applying a particle reinforcement process to the microspheres. The method may further include incorporating particulates in the microspheres prior to the sintering step to strengthen the microspheres.

A method for preparing a multi-phase scaffold for musculoskeletal tissue engineering, according to an exemplary embodiment (FIG. 4A), includes (a) processing a plurality of microspheres (step S41), including incorporating calcium phosphate into the microspheres, (b) laying the processed microspheres in a mold (step S43), wherein the microspheres in the mold presenting a gradient of microsphere sizes for a first phase and a second phase of the multi-phase scaffold, with microspheres of the first phase being in a first range of sizes, and with microspheres of the second phase being in a second range of sizes larger than the first range of sizes, (c) sintering together the microspheres in the mold above a glass transition temperature (step S45), and (d) sintering a fiber mesh, as a third phase of the multi-phase scaffold, onto the microsphere construct prepared in (c) (step S47).

Additional steps may optionally be included. For example, the method may further include seeding the third phase with at least one of fibroblasts (for example, human hamstring tendon fibroblasts), chondrocytes and stem cells. The seeding of the third phase supports growth and maintenance of soft tissue. Also, the method can include seeding the first phase with at least one of osteoblasts and stem cells. The seeding of the first phase supports growth and maintenance of bone. The method may further include seeding the second phase with at least one of chondrocytes and stem cells. Seeding of the second phase can support growth and maintenance of fibrocartilage.

The first phase may support growth and maintenance of bone. The third phase may support growth and maintenance of soft tissue. The second phase may serve at least as an interfacial zone between the first phase and the third phase.

For example, the method may further comprise seeding the first phase with first cells, for supporting growth and maintenance of the bone, seeding the third phase with second cells for supporting growth and maintenance of the soft tissue, and allowing at least some of said first cells and said second cells to migrate to the second phase.

In addition, the method may further comprise seeding at least one of said first, second and phases with one or more agents by using a microfluidic system.

Further, the method may further comprise electrospinning said fiber mesh prior to attaching the fiber mesh onto the microsphere construct.

This application also provides methods for producing polymer/ceramic composite microspheres. The composite microspheres can be formed by applying an emulsion and solvent evaporation process. The composite microspheres can comprise a degradable polymer and one of bioactive glass and calcium phosphate ceramics. The degradable polymer can be dissolved in a solvent. The bioactive glass and/or calcium phosphate ceramics can be mixed into the polymer solution. A suspension of the bioactive glass and/or calcium phosphate ceramics in the polymer solution can be poured into a stirring surfactant solution.

The degradable polymer may be a polymer selected from the group consisting at least of aliphatic polyesters, poly (amino acids), copoly(ether-esters), polyalkylenes oxalates, polyamides, poly(iminocarbonates), polyorthoesters, polyoxaesters, polyamidoesters, poly(ϵ-caprolactone)s, polyanhydrides, polyarylates, polyphosphazenes, polyhydroxylkanoates, polysaccharides and biopolymers.

Calcium phosphate and/or bioactive glass particles may be encapsulated in the microspheres during emulsion.

Figures 9A, 9B:
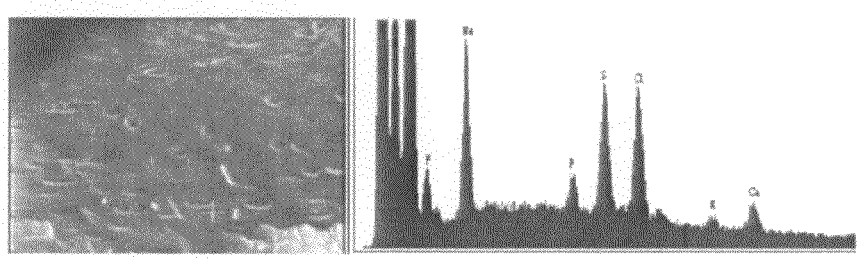
FIG. 9A: SEM of the cross section of the femoral insertion zone, 1000X.
FIG. 9B: EDAX of the femoral insertion zone. The peak intensities of Ca, P are higher compared to those in ligament region.

A method, according to another exemplary embodiment (FIG. 9B), for preparing a multi-phase scaffold for musculoskeletal tissue engineering, can comprise the steps of (a) forming a mesh scaffold by sintering together a plurality of mesh segments as a first phase of the multi-phase scaffold (step S351), (b) forming a second scaffold by sintering together a plurality of poly-lactide-co-glycolide microspheres as a second phase of the multi-phase scaffold (step S352), (c) forming a third scaffold by sintering together a plurality of microspheres formed of a composite of poly-lactide-co-glycolide and bioactive glass as a third phase of the multi-phase scaffold (step S353), and (d) sintering together said mesh scaffold, said second scaffold and said third scaffold (step S354). Steps S351 through S353 may be performed in any order.

The specific embodiments described herein are illustrative, and many variations can be introduced on these embodiments without departing from the spirit of the disclosure or from the scope of the appended claims. Elements and/or features of different illustrative embodiments may be combined with each other and/or substituted for each other within the scope of this disclosure and appended claims.

Further non-limiting details are described in the following Experimental Details section which is set forth to aid in an understanding of the invention but is not intended to, and should not be construed to, limit in any way the claims which follow thereafter.

EXPERIMENTAL DETAILS

First Set of Experiments

To address the challenge of graft fixation to subchondral bone, a normal and functional interface may be engineered between the ligament and bone. This interface, according to one exemplary embodiment, was developed from the co-culture of osteoblasts and ligament fibroblasts on a multi-phased scaffold system with a gradient of structural and functional properties mimicking those of the native insertion zones to result in the formation of a fibrocartilage-like interfacial zone on the scaffold. Variations in mineral content from the ligament proper to the subchondral bone were examined to identify design parameters significant in the development of the multi-phased scaffold. Mineral content (Ca—P distribution, Ca/P ratio) across the tissue-bone interface was characterized. A multi-phased scaffold with a biomimetic compositional variation of Ca—P was developed and effects of osteoblast-ligament fibroblast co-culture on the development of interfacial zone specific markers (proteoglycan, types II & X collagen) on the scaffold were examined.

Figures 6A, 6B:
FIGS. 6A and 6B show Bovine tibial-femoral joint after ACL and insertion site extraction (right), ACL and insertion sites after excision.
Figure 6C:
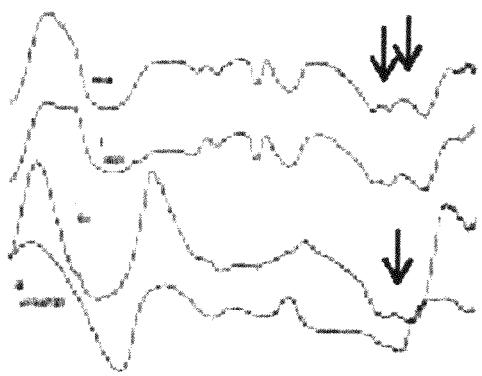
FIG. 6C shows FTIR Spectra of BG immersed in SBF for up to 7 days. Presence of an amorphous Ca—P layer at 1 day, and of a crystalline layer at 3 days.
Figure 7A:
FIG. 7A: SEM image of Ca—P nodules on BE surface (3 days in SBF). Nodules are ~1 μm in size initially, and grew as immersion continued (15,000×).
Figure 7B:
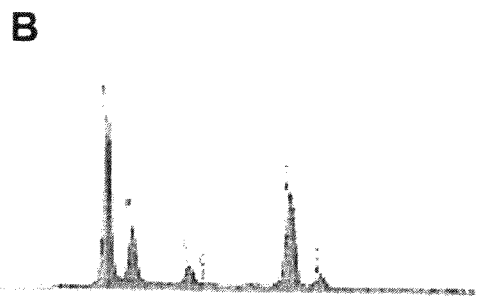
FIG. 7B: EDXA spectrum of BG surfaces immersed in SBF for 3 days. The relative Ca/P ratio is≈1.67.

The insertion sites of bovine ACL to bone (see FIGS. 5A-5C) were examined by SEM. Pre-skinned bovine tibial-femoral joints were obtained. The intact ACL and attached insertion sites were excised with a scalpel and transferred to 60 mm tissue culturing dishes filled with Dulbecco's Modified Eagle Medium (DMEM) (see FIGS. 6A and 6B). After isolation, the samples were fixed in neutral formalin overnight, and imaged by environmental SEM (FEI Quanta Environmental SEM) at an incident energy of 15 keV. ACL attachment to the femur exhibited an abrupt insertion of the collagen bundle into the cartilage/subchondral bone matrix. Examination of collagen bundle revealed that the surface was ruffled and small collagen fibrils can be seen. When a cross section was imaged, three distinct zones at the insertion site were evident: ligament (L), fibrocartilage (FC), and subchondral bone (B). The interface region spans proximally 200 μm. These cross section views showed the insertion of Sharpey fiber into the fibrocartilage (see FIGS. 6C, 7A and 7B). Mineralized fibrocartilage was not distinguishable with regular cartilage from these images.

The insertion sites of bovine ACL to bone were examined by scanning electron microscopy (SEM). Bovine tibial-femoral joints were obtained. The intact ACL and attached insertion sites were excised with a scalpel and transferred to 60 mm tissue culturing dishes filled with Dulbecco's Modified Eagle Medium (DMEM). After isolation, the samples were fixed in neutral formalin overnight, and imaged by environmental SEM (FEI Quanta Environmental SEM) at 15 keV.

Figures 8A, 8B:
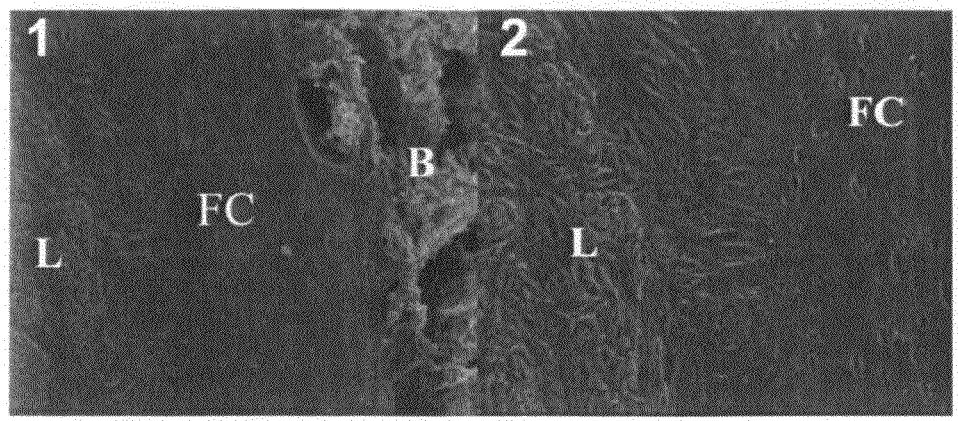
FIGS. 8A and 8B show environmental SEM images of Bovine ACL insertion Site (1 and 2), including a cross section of the ACL-femur insertion site, ACL fiber (L) left, fibrocartilage region (FC) middle, and sectioned bone (B) right (FIG. 8A: 250X.

ACL attachment to the femur exhibited an abrupt insertion of the collagen bundle into subchondral bone. When a cross section was imaged (see FIGS. 8A and 8B), three distinct zones at the insertion site were evident: ligament (L), fibrocartilage (FC), and subchondral bone (B). Sharpey fiber insertion into the fibrocartilage (see FIG. 8A) was observed. The bovine interface region spans proximally 600 μm. Examination of the interface using energy dispersive X-ray analysis (EDAX, FEI Company) enable the mineralized and non-mineralized FC zones to be distinguished. A zonal difference in Ca and P content was measured between the ligament proper and the ACL-femoral insertion (see Table I).

TABLE I

| Region Analyzed | Ca | P | Ca/P Ratio | S |
|---|---|---|---|---|
| Ligament | 1.69 | 2.98 | 0.57 | 3.71 |
| Insertion | 5.13 | 5.93 | 0.87 | 19.50 |

Figure 10:
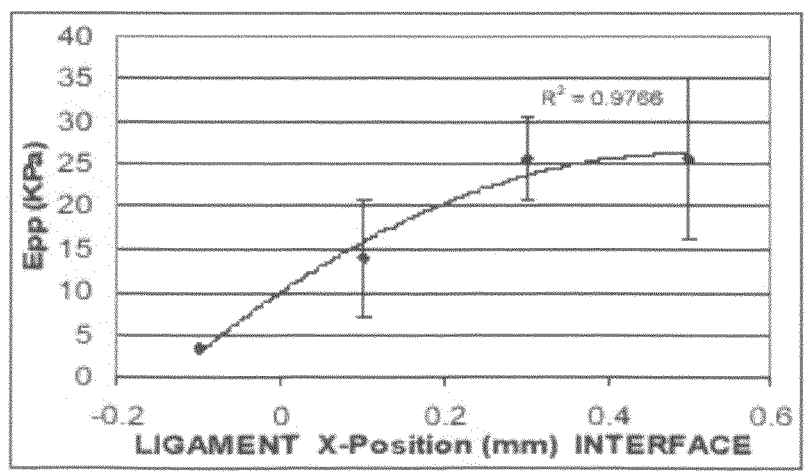
FIG. 10 shows apparent modulus versus indentation X-position across sample.

At the insertion zone (see FIGS. 9A and 9B), higher Ca and P peak intensities were observed, accompanied by an increase in Ca/P ratio as compared to the ligament region. Higher sulfur content due to the presence of sulfated proteoglycans at the FC region was also detected. The zonal difference in Ca—P content was correlated with changes in stiffness across the interface. Nanoindentation measurements were performed using atomic force microscopy (AFM, Digital Instruments). An increasing apparent modulus was measured as the indentation testing position moved from the ligament region into the transition zone (see FIG. 10).

Figures 11A, 11B:
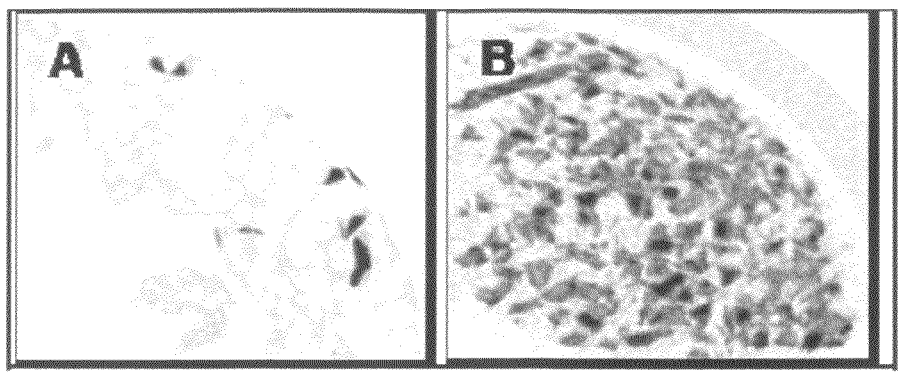
FIGS. 11A and 11B show X-Ray CT scans of discs made of poly-lactide-co-glycolide (PLAGA) 50:50 and bioactive glass (BG) submerged in SBF for 0 days (FIG. 11A) and 28 days.

Ca—P distribution on polylactide-co-glycolide (50:50) and 45S5 bioactive glass composite disc (PLAGA-BG) after incubation in a simulated body fluid (SBF) was evaluated using μCT (μCT 20, Scanco Medical, Bassersdorf, Switzerland) following the methods of Lin et al. The sample was loaded into the system, scanned at 20 mm voxel resolution and an integration time of 120 ms. FIGS. 11A and 11B compare the amount of calcified region (dark areas) observed on the PLAGA-BG disc as a function of incubation time in SBF (from day 0 to day 28). Using custom image analysis software, it was determined that at day 0, the mineralized region corresponded to 0.768% of the total disc (quartered) area, and at day 28, the mineralized region corresponded to 12.9% of the total area. Results demonstrate the Ca—P distribution on scaffolds measured by μCT analysis.

The scaffold system developed for the experiments was based on a 3-D composite scaffold of ceramic and biodegradable polymers. A composite system has been developed by combining poly-lactide-co-glycolide (PLAGA) 50:50 and bioactive glass (BG) to engineer a degradable, three-dimensional composite (PLAGA-BG) scaffold with improved mechanical properties. This composite was selected as the bony phase of the multi-phased scaffold as it has unique properties suitable as a bone graft.

A significant feature of the composite was that it was osteointegrative, i.e., able to bond to bone tissue. No such calcium phosphate layer was detected on PLAGA alone, and currently, osteointegration was deemed a significant factor in facilitating the chemical fixation of a biomaterial to bone tissue. A second feature of the scaffold was that the addition of bioactive glass granules to the PLAGA matrix results in a structure with a higher compressive modulus than PLAGA alone.

The compressive properties of the composite approach those of trabecular bone. In addition to being bioactive, the PLAGA-BG lends greater functionality in vivo compared to the PLAGA matrix alone. Moreover, the combination of the two phases serves to neutralize both the acidic byproducts produced during polymer degradation and the alkalinity due to the formation of the calcium phosphate layer. The composite supports the growth and differentiation of human osteoblast-like cells in vitro.

Figures 12A, 12B:
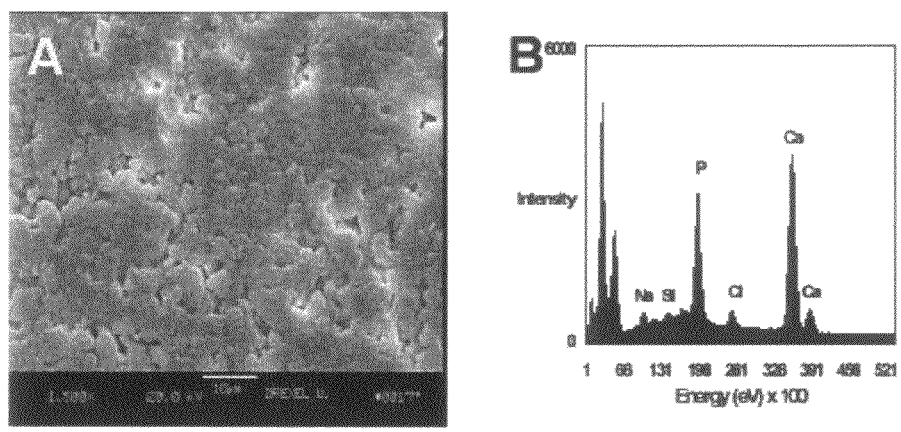
FIG. 12A: SEM image.
FIG. 12B: EDAX of PLAGA-BG immersed in SBF for 14 days.

The polymer-bioactive glass composite developed for the experiments was a novel, three-dimensional, polymer-bioactive biodegradable and osteointegrative glass composite scaffold. The morphology, porosity and mechanical properties of the PLAGA-BG construct have been characterized. BG particle reinforcement of the PLAGA structure resulted in an approximately two-fold increase in compressive modulus ($p<0.05$). PLAGA-BG scaffold formed a surface Ca—P layer when immersed in an electrolyte solution (see FIG. 12A), and a surface Ca—P layer was formed. No such layer was detected on PLAGA controls. EDXA spectra confirmed the presence of Ca and P (see FIG. 12B) on the surface. The Ca, P peaks were not evident in the spectra of PLAGA controls.

In vitro formation of a surface Ca—P layer indicates PLAGA-BG composite's osteointegrative potential in vivo. The growth and differentiation of human osteoblast-like cells on the PLAGA-BG scaffolds were also examined. The composite promoted osteoblast-like morphology and stained positive for alkaline phosphatase, and promoted synthesis to a greater extent of Type I collagen synthesis than tissue culture polystyrene controls.

Figure 13:
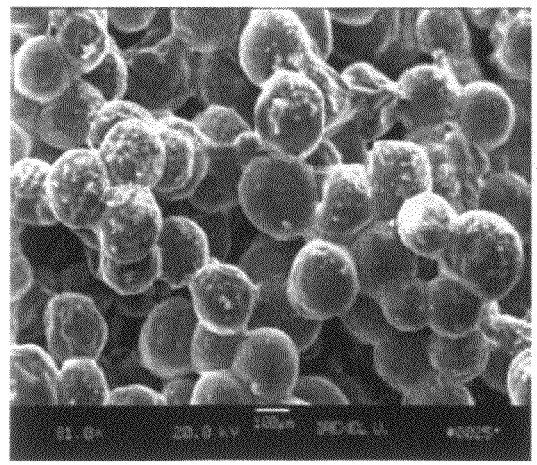
FIG. 13 shows osteoblast grown on PLAGA-BG, 3 weeks.

The porous, interconnected network of the scaffold was maintained after 3 weeks of culture (see FIG. 13). Mercury porosimetry (Micromeritics Autopore III, Micromeritics, Norcross, Ga.) was used to quantify the porosity, average pore diameter and total surface area of the composite construct. The construct porosity was determined by measuring the volume of mercury infused into the structure during analysis. In addition, the construct (n=6) was tested under compression. BG particle reinforcement of the PLAGA structure resulted in approximately two-fold increase in compressive modulus (see Table II, $p<0.05$).

TABLE II

| Scaffold Type | Average Porosity | Pore Diameter (μm) | Elastic Modulus (MPa) | Compressive Strength (MPa) |
|---|---|---|---|---|
| PLAGA | 31% | 116 | 26.48 ± 3.47 | 0.53 ± 0.07 |
| PLAGA-BG | 43% | 89 | 51.34 ± 6.08 | 0.42 ± 0.05 |

Porosity, pore diameter, and mechanical properties of the scaffold may be variable as a function of microsphere diameter and BG content. The growth and differentiation of human osteoblast-like cells on the PLAGA-BG scaffolds were also examined. The composite supported osteoblast-like morphology and stained positive for alkaline phosphatase.

The porous, interconnected network of the scaffold was maintained after 3 weeks of culture (see FIG. 13). The synthesis of type I collagen was found to be the highest on the composite, as compared to the PLAGA and tissue culture polystyrene (TCPS) controls (n=3, $p<0.05$) (see FIG. 14).

The effects of bovine osteoblast and fibroblast co-culture on their individual phenotypes were examined. The cells were isolated using primary explant culture. The co-culture was established by first dividing the surfaces of each well in a multi-well plate into three parallel sections using sterile agarose inserts. ACL cells and osteoblasts were seeded on the left and right surfaces respectively, with the middle section left empty. Cells were seeded at 50,000 cells/section and left to attach for 30 minutes prior to rinsing with PBS. The agarose inserts were removed at day 7, and cell migration into the interface was monitored. Control groups were fibroblasts alone and osteoblasts alone.

In time, both ACL fibroblasts and osteoblasts proliferated and expanded beyond the initial seeding areas. These cells continued to grow into the interfacial zone, and a contiguous, confluent culture was observed. All three cultures expressed type I collagen over time. The co-culture group expressed type II collagen at day 14, while the control fibroblast did not. Type X collagen was not expressed in these cultures, likely due to the low concentration of b-GP used. Alizarin Red S stain intensity was the highest for the osteoblast control, (see FIG. 15C) followed by the co-cultured group (see FIG. 15B). Positive ALP staining was also observed for osteoblast control and co-culture groups (see FIGS. 16C and 16B, respectively).

Scaffold of four continuous, graded layers with different sizes of microspheres was formulated (see FIGS. 17A-17F). Layered inhomogeneity was pre-designed into the scaffold. Due to differences in packing efficiency between different sizes of microspheres, the porosity of the scaffold decreases from layers of large microsphere to those consisting of small microspheres. PLAGA-BG composite microspheres were produced via the emulsion method. Three layers of PLAGA-BG microspheres of different diameters (250-300, 300-355, 355-500 μm, from top to bottom) were used, shown in FIGS. 17A-17F. Microsphere layers were sintered at 70° C. for 20 hours.

Image analysis confirmed that pore size increased from bottom to top of scaffold. For the growth of ACL fibroblasts on the scaffold, another type of multi-phased scaffold was fabricated using a PLAGA mesh (Ethicon, N.J.) and two layers of PLAGA-BG microspheres. The layers were sintered in three stages in a Teflon mold. First the mesh was cut into small pieces and sintered in the mold for more than 20 hours at 55° C. A layer of PLAGA-BG microspheres with diameter of 425-500 μm was then added to the mold. This layer was sintered for more than 20 hours at 75° C. The final layer consisted of PLAGA-BG microspheres with diameter greater than 300 μm. The scaffolds and three distinct regions were readily observed (see FIGS. 18A-18C).

Kinetics of Ca—P layer formation on BG surfaces was related to changes in surface zeta potential in a simulated body fluid (SBF). The chemical and structural changes in BG surface Ca—P layer were characterized using Fourier transform infrared spectroscopy (FTIR), SEM and energy dispersive x-ray analysis (EDXA). FTIR provides information on the degree of crystallinity (amorphous vs. crystalline) of the Ca—P layer formed (see FIG. 6) as well as the functional groups present on BG surface (carbonated Ca—P layer versus non-carbonated, protein adsorption, etc.). FTIR is much more surface sensitive than X-ray diffraction in detecting the Ca—P crystalline structures when the surface layer is only several microns in thickness. SEM combined with EDXA is a powerful tool in relating elemental composition to specific surface morphology and distributions (see FIGS. 7B and 7C). EDXA provides a direct calculation of Ca/P ratio (Ca/P=1.67 for bone mineral and crystalline Ca—P layer) when appropriate standards are used. FTIR, SEM, and EDXA are complimentary techniques which together provide quantitative data on the crystallinity, composition of and functional groups pertaining to the Ca—P layer.

Evaluation of the effects of co-culturing on the growth and phenotypic expression of osteoblasts and chondrocytes. Osteoblasts were seeded directly on high density chondrocyte micromasses. Specific effects of co-culture on the expression of chondrogenic markers were observed primarily at the top surface interaction zone instead of within the micromass. Alcian blue staining (see FIG. 19B) revealed characteristic peri-cellular sulfated GAG deposition by chondrocytes. GAG deposition was found largely within the micromass, instead of at the co-culture zone where elongated osteoblasts and chondrocytes were located. Sulfated GAG was not detected in the predominantly osteoblast monolayer surrounding the micromass. Surface chondrocytes may have de-differentiated due to co-culturing with osteoblasts. The expression of type I collagen was observed to be distributed mainly on the top surface of the co-cultured mass (FIG. 19C), where osteoblasts were located. Type I was also found at the primarily osteoblastic monolayer surrounding the micromass (see FIG. 19C, left). No type I collagen expression was observed in the chondrocyte-dominated center and bottom surface of the micromass. High expression of type II collagen was observed within the micromass (see FIG. 19D).

As types I and II collagen were detected at the surface, it is possible that due to co-culture, chondrocytes and osteoblasts were forming an osteochondral-like interface at the surface interaction zone. Alizarin Red (ALZ) staining revealed that there was limited mineralization in the co-cultured group, while the osteoblast control stained increasingly positive for calcium. It is likely that co-culture with chondrocytes may have delayed osteoblast mineralization. Preliminary PCR results (see FIGS. 20A and 20B) showed that the 7 day co-culture group expressed types II and X collagen, as detected by RT-PCR.

Effects of media additives on the growth and mineralization of osteoblasts and human ACL fibroblasts (hACL) were examined. During mineralization, ALP reacted with β-glycerophosphate (βGP) and the phosphate product was utilized for mineralization. Concentrations (0, 1.0, 3.0, 5.0 mM) effects were examined over time. No significant change in cell number was observed for the [βGP] investigated. At 1.0 mM, a significant difference between 1-day & 7-day samples ($p<0.05$) was observed. No differences were found between 1.0 mM and 3.0 mM cultures. ALZ stains for the osteoblast cultures were more intense for 3.0 mM than for 1.0 mM. Ectopic mineralization was observed for hACL cultures at 3.0 mM suggesting a potential change in cell phenotype.

Interaction of osteoblasts and chondrocytes on a 3-D composite scaffold during co-culture was examined. Scaffolds seeded with only osteoblasts or chondrocytes at the same densities served as controls. Both short-term and long-term co-culture experiments were conducted. Extensive SEM analysis revealed that significant interactions occurred between osteoblasts and chondrocytes during co-culture. Differences in cellular attachment were observed between the chondrocyte control scaffolds and the co-cultured scaffolds. On the co-cultured scaffolds, focal adhesions were evident between the spherical chondrocytes and the surface, indicated by the arrow in FIG. 21B.

No comparable focal adhesions were observed on the chondrocyte controls at the same time point. Chondrocyte morphology changed over time as it assumed a spherical morphology in the first 8 hours, and then spread on the surface of the microspheres (see FIG. 22A). The nodules on the surface of the microspheres correspond to the flattened chondrocytes. These nodules were likely chondrocytes instead of calcium phosphate nodules, since calcium phosphate nodules were approximately 1-5 µm in diameter at the culture duration observed and these nodules were ~10 µm, approximately the diameter of an ovoid cell. After 7 days of culture, the co-culture group exhibited extensive matrix production (see FIG. 22C) and expansion on the scaffold.

Examination of the ACL-bone interface confirmed existence of a mineral gradient across the insertion zone and correlation to changes in material properties. Multi-phased scaffolds with controlled morphology and porosity were fabricated. The osteochondral graft developed from co-culture on PLAGA-BG and hydrogel scaffold supported growth of multiple matrix zones with varied GAG and mineral content. BMSCs differentiated into ligament fibroblast and produced a functional extracellular matrix when cultured with growth factors on a fiber-based scaffold. Mineral content, distribution, and chemistry at the interface and on the scaffold were quantifiable using a complimentary set of surface analysis techniques (FTIR, SEM, EDAX, µCT). Electron microscopy examination of the ACL-bone interface revealed insertion zone including three different regions: ligament, fibrocartilage-like zone, and bone. Co-culture of osteoblasts and ligament fibroblasts on 2-D and 3-D scaffolds resulted in changes in cell morphology and phenotype. Type X collagen, an interfacial zone marker, was expressed during co-culture. Multiphased scaffold with layered morphology and inhomogenous properties were designed and fabricated. FTIR, SEM and EDXA are complimentary techniques which collectively provided qualitative and quantitative information on the Ca—P layer and composition of the calcium phosphate surface.

Second Set of Experiments

Figure 24:
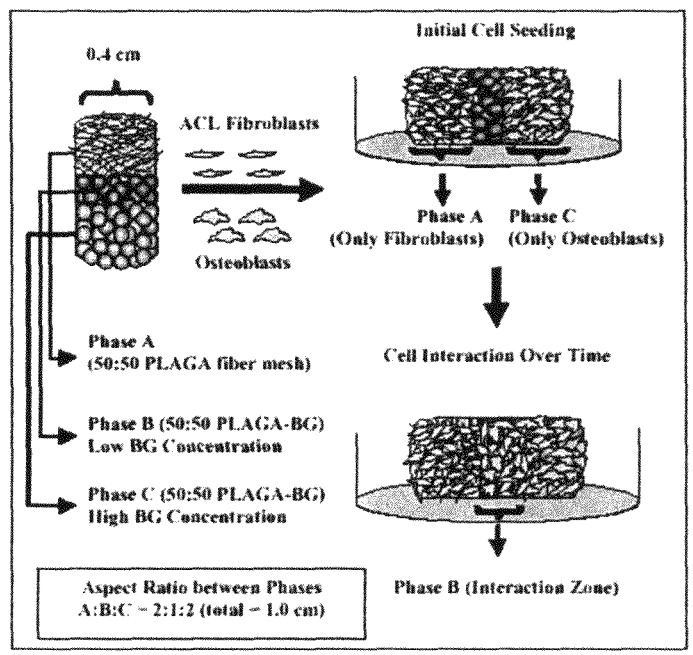
FIG. 24 shows multi-phased scaffold, according to one embodiment (for in vitro co-culture).

A multi-phased scaffold system with inhomogenous properties (FIG. 24) was designed and evaluated for its ability to support the growth and differentiation of multiple cell types. Effects of osteoblast-ligament fibroblast co-culture on a development of interfacial zone specific markers (proteoglycan, types II & X collagen) on the scaffold were examined.

The contiguous scaffold included three sequential phases (A-C), with Phase A (polymer fiber mesh with no Ca—P) intended for ligament culture, and Phase C (polymer-ceramic composite with high Ca—P) for bone formation. Phase B (polymer-ceramic composite, lower Ca—P than Phase C), the intermediate region, was where an interfacial zone developed due to the interaction of these two cell types. The scaffolds were fabricated from PLAGA 50:50, and the same polymer was used throughout. The three phases were sintered together past a polymer glass transition temperature to form a multi-phased scaffold. The aspect ratio between the phases of the sintered cylindrical scaffold was as follows: A:B:C=2:1:2, and the as-made, complete construct was 1.0 cm in length and 0.40 cm in diameter (see FIG. 24).

The mineral gradient was created by incorporating different concentrations of bioactive glass (BG) particles during the microsphere synthesis process. BG wt % was correlated to the Ca—P content of the interface by comparative EDXA analysis of the Ca—P surface developed through immersion in a simulated body fluid following a well-characterized method to create Ca—P layer on bioactive glass surfaces as described by Lu et al. (2000) and incorporated by reference herein.

When a specific BG wt % was correlated with the Ca—P distribution and Ca/P ratio of either the bone or the cartilage region as described above, scaffolds were fabricated based on this wt %.

The three phases of the scaffold were inhomogeneous in properties, with zonal differences in mineral content and matrix morphology (see Table III).

TABLE III

| | Phase A (Ligament) | Phase B (Interface) | Phase C (Bone) |
|---|---|---|---|
| Composition | PLAGA 50:50 (no BG) | PLAGA 50:50/BG (lower) | PLAGA 50:50/BG (higher) |
| Porosity/Pore Diameter | 40%, 100 µm | 40%, 100 µm | 40%, 100 µm |
| Matrix Morphology | Fiber Mesh | Microsphere Based | Microsphere Based |

The differences mimic the ACL-bone interface and facilitate the growth of different tissues. Phase C has a high mineral content compared to Phase A. While the three phases share the same polymer composition, they differ in weight % of BG. A positive correlation exists between scaffold stiffness and mineral content of the phase.

The three phases also differ in morphology, with Phase A composed of a porous fibrous mesh, and Phases B and C made of microsphere-based porous scaffold. Post-fabrication characterization of the scaffold included porosity, average pore size, total surface area, as well as mechanical properties under compression. Scaffold porosity was held constant at 40% with a pore diameter of 100 µm, with focus on the effect of mineral content on cellular response as a more relevant parameter in controlling fibroblast phenotype or dedifferentiation into chondrocytes. Growth and differentiation of osteoblasts and ligament fibroblasts co-cultured on the scaffold were examined. Osteoblasts were seeded on Phase C while ligament fibroblasts were seeded on Phase A.

The growth and differentiation of cells on the scaffold was monitored as a function of culturing time (1, 3, 7, 14, 21 days). Cell proliferation, ligament phenotypic expression (fibronectin, type I, III, II collagen synthesis, laminin, fibronectin) and osteoblast phenotype (alkaline phosphatase, type I collagen, osteocalcin, mineralization) were examined. Expression of interface-specific markers such as proteoglycans, types II and X collagen were determined to assess changes in fibroblast phenotype.

The three phases of the scaffold differed in composition and morphology, while the same porosity and pore diameter were maintained. Focus was placed on the mineral content of the scaffold for two reasons: 1) it is a more relevant parameter for consideration of the varied mineral distribution within the ACL-bone interface; and 2) mineral content was utilized to direct fibroblast phenotype change or dedifferentiation into chondrocytes.

A component of the polymer ceramic composite scaffold was polylactide (PLA) which degrades via hydrolysis into lactic acid, which may contribute to changes in ligament fibroblast phenotype. Increased mineralization by ligament fibroblasts was observed with increasing concentration of β-glycerophosphate, a media additive commonly used in osteoblast cultures.

The effects of co-culture were evaluated in conjunction with scaffold mineral content. Multiple cell types were considered because the insertion site was made up of four zones, each dominated by a specific cell type. Cell to cell interactions played a significant role in dictating the formation of the interface between ligament and bone. Examination of osteoblast and ligament fibroblast co-cultures established that both cell types proliferated and expanded beyond the initial seeding areas, and that a contiguous and confluent culture was observed at the interface after two weeks. Preliminary studies revealed that co-culture and/or interactions with chondrocytes may have delayed osteoblast-mediated mineralization. Type X collagen was found in the osteoblast-chondrocyte co-cultured samples.

Third Set of Experiments

An objective of the experiments (described below) was to develop a three-dimensional (3-D), porous composite of polylactide-co-glycolide (PLAGA) and 45S5 bioactive glass (BG) that is biodegradable, bioactive, and suitable as a scaffold for bone tissue engineering (PLAGA-BG composite). Additional objectives of the study were to examine the mechanical properties of a PLAGA-BG matrix, evaluate the response of human osteoblast-like cells to the PLAGA-BG composite, and evaluate the ability of the composite to form a surface calcium phosphate layer in vitro. Structural and mechanical properties of PLAGA-BG were measured, and the formation of a surface calcium phosphate layer was evaluated by surface analysis methods. The growth and differentiation of human osteoblast-like cells on PLAGA-BG were also examined. The addition of bioactive glass granules to the PLAGA matrix resulted in a structure with higher compressive modulus than PLAGA alone. Moreover, the PLAGA-BA composite was found to be a bioactive material, as it formed surface calcium phosphate deposits in a simulated body fluid (SBF), and in the presence of cells and serum proteins. The composite supported osteoblast-like morphology, stained positively for alkaline phosphatase, and supported higher levels of Type I collagen synthesis than tissue culture polystyrene controls. A degradable, porous, polymer bioactive glass composite possessing improved mechanical properties and osteointegrative potential compared to degradable polymers of poly(lactic acid-glycolic acid) alone was successfully developed.

Figure 25:
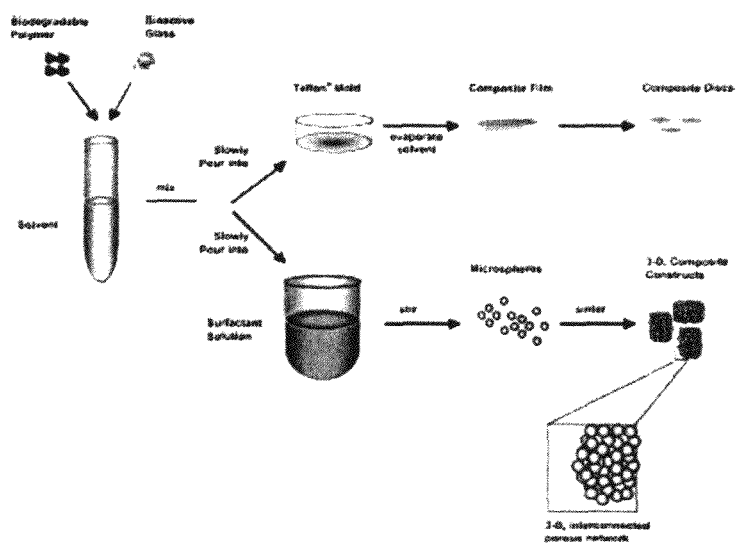
FIG. 25 shows a schematic diagram depicting a fabrication process of a composite (PLAGA-BG) of PLAGA and BG, in thin film form and as a 3-D, porous scaffold.

Polylactide-co-glycolide 50:50 co-polymer (PLAGA, Mw≈50,000, American Cyanamide, Sunnyvale, Calif.) and 45S5 bioactive glass (BG, MO-SCI Corporation, Rolla, Mo.) granules were used to fabricate the composite (PLAGA-BG) discs and microspheres. FIG. 25 is a schematic of the synthesis process of some forms of PLAGA-BG composite used in this study. Specifically, PLAGA-BG discs were formed through the traditional solvent-casting process, where PLAGA and BG granules were first mixed according to a polymer to ceramic weight ratio of 1:3 and dissolved in methylene chloride. The solution was then slowly poured into a Teflon mold and allowed to cool overnight in a −20° C. freezer. The resultant polymer-ceramic film was bored into 1-cm wide and 0.1-mm thick discs. The discs were then dried overnight to remove any residual solvent (Lyph-lock 12, Labconco, Kansas City, Kans.).

PLAGA-BG composite microspheres were formed through a water-oil-water emulsion. Specifically, PLAGA granules were first dissolved in methylene chloride, and BG particles (<40 μm) were added to achieve a 25% mixture. The mixture was then poured into a 1% polyvinyl alcohol (Polysciences, Warrington, Pa.) solution. The suspension was stirred constantly, and the spheres were allowed to harden in the polyvinyl alcohol solution. The resultant microspheres were then washed, vacuum filtered, and dried at room temperature. Next, the composite microspheres were sifted using a mechanical sifter to a final size range of 100-200 μm. The cylindrical construct, averaging 0.5 cm in width and 1.0 cm in height, was fabricated by heating the microspheres at 70° C. for 20 h in a stainless-steel mold.

Before in vitro evaluations, the morphology, porosity and mechanical properties of the PLAGA-BG construct were determined. Pore interconnectivity, morphology, and the bonding of microspheres within the construct was examined by scanning electron microscopy (SEM, Amray 1830-D4), at an acceleration voltage of 20 keV. Elemental composition of the composite surface was determined by energy-dispersive X-ray analysis (EDXA). Mercury porosimetry (Micromeritics Autopore III, Micromeritics, Norcross, Ga.) was used to measure the porosity, average pore diameter, and total surface area of the composite construct. In this method, the construct porosity was determined by measuring the volume of mercury infused into the structure during analysis. In addition, the construct (n=6) was tested under compression using the Instron Servohydrolic System 8500 (Instron, Canton, Mass.), with a ramp speed of 0.02 cm/s. The compressive strength and elastic modulus of the construct were determined. PLAGA scaffolds without BG served as controls.

The composite discs were immersed for 1, 7, and 14 days in a simulated body fluid (SBF) whose ion concentration is similar to that of extracellular fluid. PLAGA discs without BG served as controls. A surface area to volume ratio of 1.0 cm-1 was maintained for all immersions. The pH of the solution as a function of immersion time was measured. Perfect sink conditions were maintained during the immersion study. SEM (Amray 1830-D4) and EDXA were used to monitor the formation of a Ca—P layer on composite films.

Human osteosarcoma cells (SaOS-2) were cultured in Medium 199 (M199, Sigma Chemicals, St. Louis, Mo.), supplemented with 10% fetal bovine serum (Life Technologies, Rockville, Md.), L-glutamine, and antibiotics. The cells were grown to confluence at 37° C. and 5% CO2. Under these conditions, the osteoblastic phenotype of SaOS-2 was maintained for up to at least four weeks of culture, with positive expression of alkaline phosphatase, type I collagen, osteocalcin, and formation of mineralized cultures.

SaOS-2 cells were seeded on the porous, PLAGA-BG scaffolds (n=3) at the density of 5×104 cells/cm2, and were cultured in 12-well plates (Fisher Scientific, Fair Lawns, N.J.) for up to 3 weeks. PLAGA alone and tissue culture polystyrene (TCPS) served as control groups. Once the cells have grown to confluence, at two weeks from the start of culture, mineralization medium containing 3.0 mM of β-glycerophosphate and 10 μg/ml of L-ascorbic acid were added to the culture.

Cell adhesion and growth morphology on the 3-D construct were monitored using SEM (20 keV). Alkaline phosphatase staining was performed at each culturing time point, using a standard histochemical assay. The samples were incubated for 30 min with Napthol AS-Bi (Sigma), phosphate salt, N,N-dimethyl formamide (Sigma), and Fast Red (Sigma) at 37° C. The samples were then fixed in 2% paraformaldehyde for 30 min at 4° C. The synthesis of type I collagen by SaOS-2 cells was quantified using a modified ELISA.

The formation of mineralized nodules was examined by SEM-EDXA. Mineralization was further ascertained using Alizarin Red S staining for calcium. Briefly, the samples were washed with deionized H2O, fixed with 2% paraformaldehyde and incubated in 2% Alizarin Red S solution for 5 min. The samples were then washed with deionized water and viewed under the microscope.

Data in the graphs are presented in the form of mean±standard deviation (mean±SD), with n equal to the number of samples analyzed per immersion treatment. One-way analyses of variance (ANOVA) and the Student's t-test were used to compare the mechanical testing data (n=6), porosimetry results (n=3), as well as the collagen synthesis data (n=3). Statistical significance was evaluated at the $p<0.05$.

SEM examination of the PLAGA-BG discs revealed a homogenous distribution of the BG particles within the PLAGA phase. In addition, the composites in disc form as well as microsphere form were visually more opaque than PLAGA alone, largely because of the addition of BG. Sintering of the microspheres resulted in a well-integrated structure, with the microspheres joined at the contact necks. SEM analysis revealed that a 3-D, interconnected porous network was found throughout the composite construct. Elemental analysis using EDXA showed that the composite surface was largely made up of C, Na, Si, Ca, and P before any immersions.

FIG. 23 shows a table which summarizes the result from structural characterizations of the as-fabricated composite scaffold. BG particle-reinforcement of the PLAGA structure resulted in a near two-fold increase in compressive modulus. The structural and mechanical properties of the scaffold can be systematically optimized by varying microsphere and scaffold fabrication parameters. Porosimetry analysis revealed that the 3-D composite measured an average porosity of 43%, with a mean pore diameter of 89 μm. The PLAGA control scaffold exhibited 31% total porosity and a mean pore diameter of 116 μm. The PLAGA-BG composite possessed a higher elastic modulus (51.336±6.080 MPa versus 26.479±13.468 MPa) than the control PLAGA scaffold. Although the means were different, the compressive strength of the composite at 0.417±0.054 MPa was not statistically different from that of the PLAGA control (0.533±0.068 MPa), at $p<0.05$.

The bioactivity of the composite was determined by monitoring the formation of a calcium phosphate layer on the composite discs in a SBF. The composite was found to be bioactive because it formed a calcium phosphate layer on its surface after immersion in SBF for 7 days. SEM-EDXA results showed that an amorphous calcium-phosphate layer was found on the composite surface after 7 days of immersion, whereas no such layer was detected on the control polymer without bioactive glass particles for the same duration. In particular, polymer-ceramic composite (PLAGA-BG) which were immersed in simulated body fluid (SBF) for 14 days formed a surface calcium phosphate layer (Ca, P presence confirmed by X-ray analysis as summarized in FIG. 26). No such layer was found on the PLAGA control without 45S5 bioactive glass. The composite (PLAGA-BG) surface was covered with calcium phosphate nodules after 14 days of immersion. In contrast, the PLAGA control surface, after immersion for 14 days in SBF, did not form a calcium phosphate layer, but began to exhibit surface pores formed due to the degradation of the polymer.

Figure 26:
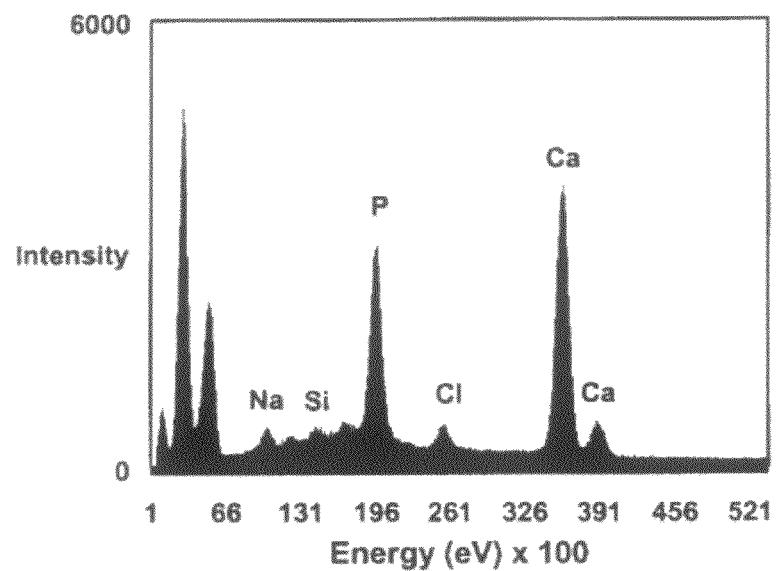
FIG. 26 shows EDXA spectra of the PLAGA-BG composite immersed in a SBF for 14 days.

FIG. 26 shows EDXA spectra of the PLAGA-BG composite immersed in a SBF for 14 days. The composite surface still contained C, Si, Ca, and P, whereas the Cl peak was detected after immersion in SBF. A surface calcium phosphate layer has formed on the PLAGA-BG composite surface. The Ca and P peaks were not found in the spectra of PLAGA controls.

The microsphere-based, porous, PLAGA-BG composite supported the growth and phenotypic expression of human osteoblast-like cells. Media pH variation was measured for the full duration (3 weeks) of cell culture with PLAGA-BG and PLAGA, and physiological pH (7.3-7.7) was maintained in all cultures for up to 3 weeks. There was no significant change in solution pH after 2 weeks of culture with osteoblast-like cells, and culture media was exchanged every other day to remove metabolic products and supply fresh nutrients to the cells. Extensive cellular growth was detected on the scaffold surface as well as within the PLAGA-BG composite. In addition, the porous network of the scaffold was maintained even after 3 weeks of culture. In many areas, cellular growth had bridged two or more microspheres while maintaining the porous structure. SEM analysis revealed the synthesis of collagen-like fibers by the SaOS-2 cells. All cultures stained positively for the synthesis of alkaline phosphatase, although a much higher intensity of stain was observed in cultures with the PLAGA-BG scaffold than for PLAGA cultures.

Figure 27:
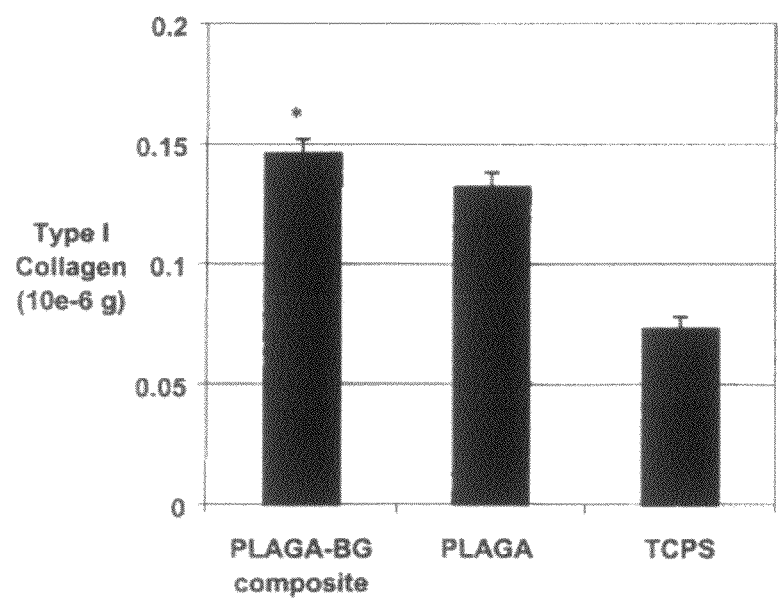
FIG. 27 shows a comparison of the expression of type I collagen by human osteoblast-like cells cultured on the PLAGA-BG composite versus on TCPS controls and on PLAGA alone.

As shown in FIG. 27, the synthesis of type I collagen by SaOS-2 cells increased with culturing time, with the highest amount found on PLAGA-BG composite (0.146±0.006 μg), as compared to PLAGA (0.132±0.006 μg), and TCPS controls (0.073±0.005 μg). The expression of type I collagen by SaOS-2 cells cultured on the composite was significantly higher than cells grown on TCPS controls, ($p<0.05$). There was a trend towards higher Type I collagen synthesis on the PLAGA-BG composite compared to PLAGA alone, but this was not found to be significant. ($p=0.06$) The formation of a mineralized matrix was confirmed by positive staining with Alizarin Red S and elemental analysis in which Ca and P were detected on PLAGABG scaffolds cultured with SaOS-2 cells. Alizarin stain intensity increased with culturing time. The mineralized nodules were not observed on PLAGA or TCPS controls after 2 weeks of culture, before the addition of the mineralization medium. After 1 week of culturing with the mineralization medium, mineralization as reflected in staining intensity, was much less on the control substrates than on PLAGA-BG.

SEM and EDXA analyses confirmed the formation of calcium phosphate nodules on the composite surface after only 3 days of culture, before the addition of the mineralization medium. These calcium phosphate nodules are similar in size and shape as observed on PLAGA-BG discs in the SBF. In time, the Ca—P nodules increased in size and formed larger aggregates, indicating that the PLAGABG composite was bioactive in vitro. The relative Ca to P peak ratio of the deposits decreased as a function of culturing time. These results collectively suggest that the composite was bioactive, and was capable of forming a surface calcium phosphate layer.

Fourth Set of Experiments

The degree of graft integration is a significant factor governing clinical success and it is believed that interface regeneration significantly improves the long term outcome. The approach of this set of experiments was to regenerate the ACL-bone interface through biomimetic scaffold design and the co-culture of osteoblasts and fibroblasts. The interface exhibits varying cellular, chemical, and mechanical properties across the tissue zones, which can be explored as scaffold design parameters. This study describes the design and testing of a multi-phased, continuous scaffold with controlled heterogeneity for the formation of multiple tissues. The continuous scaffold consists of three phases: Phase A for soft tissue, Phase C for bone, and Phase B for interface development. Each phase was designed with optimal composition and geometry suitable for the tissue type to be regenerated. Fibroblasts were seeded on Phase A and osteoblasts were seeded on Phase C, and the interactions of osteoblasts and fibroblasts (ACL and hamstring tendon) during co-cultures on the scaffolds were examined in vitro.

Phases A, B and C consist of poly(lactide-co-glycolide) (PLAGA, 10:90) woven mesh, PLAGA (85:15) microspheres, and PLAGA (85:15)/Bioactive Glass (45S5, BG) composite microspheres, respectively. The microspheres were formed via a double emulsion method, and the continuous multi-phased scaffolds were formed by sintering above the polymer $T_g$. Scaffold porosity and pore diameter were determined by porosimetry (Micromeritics, n=3) and the samples were tested under uniaxial compression (MTS 810, n=5) at 1.3 mm/min up to 5% strain with 10 N preload.

Bovine and human osteoblasts (bOB and hOB), and bovine ACL fibroblasts (bFB) and human hamstring tendon fibroblasts (hFB) were obtained through explant culture. In experiment I, bOB and bFB ($5\times10^5$ cells each/scaffold) were co-cultured on the scaffold, and cell viability, attachment, migration and growth were evaluated by electron and fluorescence microscopy. The bOB were pre-labeled with CM-DiI, and both cell types were labeled with calcein AM (Molecular Probes) prior to imaging. Matrix production and mineralization were determined by histology. After ascertaining cell viability on the scaffolds, a more extensive experiment using hOB and hFB was conducted in which cell proliferation and differentiation and above analyses were investigated. The mechanical properties of the seeded scaffolds were also measured as a function of culture time.

Compression testing of scaffolds indicated an average modulus of 120±20 MPa and yield strength of 2.3 MPa. The intrusion volume, porosity and pore diameter data are summarized in the table shown in FIG. 28-1.

The fibroblasts and osteoblasts were localized primarily at the two ends of the scaffolds after initial seeding, with few cells found in Phase B. After 28 days, both cell types migrated into Phase B (FIG. 28-2B), and extensive cell growth was observed in Phases A and C (FIGS. 28-2A and 28-2C).

Figures 1, 2, 3A, 3B, 3C, 3D, 33:
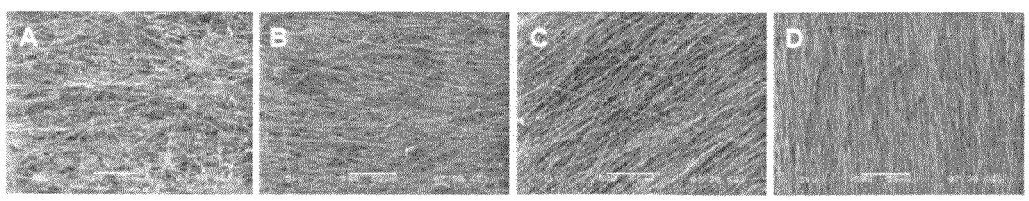

Extensive collagen-rich matrix production was found throughout the three phases at day 28 (FIGS. 28-3A and 28-3B).

The biomimetic, multi-phased scaffolds supported the growth and ECM production of both osteoblasts and fibroblasts. After 28 days of culture, collagen production was evident in all three phases and mineralized matrix was found in the bone and interface regions. Osteoblast and fibroblast interaction at the interface (Phase B) suggests that these cells may play a significant role in the development of a functional insertion site. These findings demonstrate that this novel scaffold is capable of simultaneously supporting the growth of multiple cell types and can be used as a model system to regenerate the soft tissue to bone interface. Additional studies can focus on scaffold optimization and the development of the interface on the novel scaffold.

Fifth Set of Experiments

This set of experiments is directed to the development of a multi-phased scaffold with controlled heterogeneity for interface tissue engineering. This continuous scaffold is comprised of three phases with Phase A designed for ligament formation, Phase C for bone, and Phase B for interface development. The design objective was to formulate a scaffold that is able to support the growth and differentiation of both osteoblasts and ligament fibroblasts. Two design parameters were varied among the three phases: mineral (Ca/P) content and geometry. This study introduces a 3-D biomimetic substrate for interface development. The interaction of osteoblasts and ACL fibroblasts during co-culture on the multi-phased scaffold were examined. An objective of the study was to demonstrate that both cell types proliferate and elaborate a collagen like matrix on the 3-D scaffolds.

Two types of scaffolds were fabricated. The first type is comprised entirely of microspheres formed via a double emulsion method. Phase A consists of poly(lactide-co-glycolide) 50:50 (PLAGA), Phase C of PLAGA/Bioactive glass (PLAGA-BG) composite microspheres, and Phase B contains a mixture of PLAGA and PLAGA-BG. For the second type of scaffold which has a different geometry and degradation rate, Phase A consists of PLAGA (10:90) woven mesh, Phase C of PLAGA 85:15/BG microspheres, and Phase B contains PLAGA (85:15) microspheres. The continuous multi-phased scaffolds were formed by sintering above the glass transition temperature.

Bovine osteoblasts and ACL fibroblasts were obtained from explant cultures of tissue isolated from neonatal calves. The cells were cultured in Dulbecco's Modified Eagles Medium (DMEM, Mediatech), supplemented with 10% fetal bovine serum, L-glutamine, and 1% penicillin/streptomycin (Mediatech).

Scaffolds were sterilized by ethylene oxide and fibroblasts were seeded at a density of $5\times10^5$ cell/scaffold onto Phase A, while osteoblasts were seeded at $5\times10^5$ cell/scaffold on Phase C. Phase B was left unseeded and the migration of osteoblasts and fibroblasts into this interfacial region was examined. The osteoblasts were labeled with CM-DiI cell tracer (Molecular Probes), and their location was tracked with respect to fibroblasts and each phase of the scaffold. The scaffolds were cultured in supplemented DMEM for up to 28 days. Ascorbic acid (10 µg/mL) and 3 mM β-glycerophosphate were added to the cultures at day 7.

Cell migration, attachment and growth were examined using scanning electron microscopy (5 kV, JEOL 5600LV). Cell viability and migration were evaluated by fluorescence microscopy (Zeiss Axiovert 40) using calcein AM tracer (Molecular Probes). Matrix production and mineralization were determined via histology. The samples were fixed, embedded and sectioned, after which Trichrome, von Kossa and Picrosirius Red stains were performed.

At day 0, SEM analysis showed that a large number of cells attached to Phase A and C of the scaffolds (FIG. 29-1A). Fluorescence microscopy revealed that fibroblasts and osteoblasts were localized primarily at opposite ends of the scaffolds after initial seeding, with very few cells found in Phase B (FIGS. 29-2A through 29-2C). At day 28, SEM analysis revealed that both cell types elaborated extracellular matrix (ECM) on Phases A and C (FIGS. 29-1B and 29-1C) with some matrix formation observed in Phase B (FIG. 29-1D). Fibroblasts were found largely in Phase A and osteoblasts in Phase C (FIGS. 29-2D and 29-2F), with a mixture of cell types found in Phase B (FIG. 29-2E).

Histological analyses confirmed cell migration into Phase B and matrix production throughout the three phases of the scaffold at day 28 (FIGS. 29-3A1 through 29-3A3). The collagen-rich matrix (FIGS. 29-3B1 and 29-3B2) seen in all three phases and osteoblast-mediated mineralization were observed on the surface of the PLAGA-BG microspheres (FIG. 29-3C, see arrow).

The biomimetic, multi-phased scaffolds supported the growth and ECM production by both osteoblasts and fibroblasts. After 28 days of culture, collagen production was evident in all three phases and mineralized matrix was found in the bone and interface regions only. Osteoblast and fibroblast interaction at the interface (Phase B) suggests that these cells may serve a significant role in the development of a functional insertion site. The results demonstrate that this novel scaffold is capable of simultaneously supporting the growth of multiple matrix zones. Additional studies can examine the effects of cell-cell interactions at the interface region and optimize the scaffold for clinical utilization.

Sixth Set of Experiments

It is believed that fibroblasts and osteoblasts interactions play a significant role in interface formation. In vivo, fibroblasts and osteoblasts form a fibrocartilage layer within the bone tunnel. Since the natural interface spans less than 400 μm, a novel micro-co-culture model was developed that utilizes microfluidics to exert spatial control in cell distribution. This can be used to determine how cell-cell interactions may regulate interface remodeling locally at the micro-scale. The fabrication parameters of this model were optimized and initial osteoblastic and fibroblastic responses were examined.

Channels were designed having a bimodal non-intersecting serpentine geometry with 200 μm features. The design was implemented on silicon wafers using SU-8 25 (Microchem) photoresist and a mold patterned using Polydimethylsiloxane (PDMS, Dupont). In this design, osteoblast and fibroblast channels were first separated by PDMS, which was later removed to allow cell to cell interactions.

In order to optimize the channel depth for subsequent co-culture studies, the spin-coating durations (30, 45, 60 and 90 s) were varied. Cell seeding time was optimized by incubating the cells within the channels for 1, 3, 6, and 24 hours prior to removal of the PDMS followed by live-dead staining.

Bovine primary osteoblasts and fibroblasts were obtained from explant cultures. The cells were grown in supplemented DMEM (10% FBS, 1% NEAA and 1% antibiotics) at 37° C. and 5% $CO_2$. Osteoblast or fibroblast suspension ($20 \times 10^6$ cells/ml) was perfused into its respective microchannels. Cells were allowed to attach for 1 hr prior to PDMS removal. Cell migration was tracked by labeling fibroblasts with CM-DiI and osteoblasts with CFDA-SE (Molecular Probes) prior to seeding.

Analyses were performed at days 1, 2, and 6 following PDMS removal. Alkaline Phosphatase (ALP) activity was ascertained with fast-blue stain (Sigma), while type-I collagen deposition was examined by immunohistochemistry.

A spin-coating duration of 30 s was chosen to balance channel depth and uniformity. Based on the cell viability, the optimal cell attachment time within the channels was 1 hr (FIG. 30-2a). Both cell types migrated and proliferated beyond their initial seeding zone (FIGS. 30-1a through 30-1d) and grew into physical contact by day 1 (FIGS. 30-1e and 30-1f). Local confluency and cross-migration were observed at day 2. ALP activity was observed in the osteoblast region (FIG. 30-2b), while type-I collagen was found in all regions (FIG. 30-2c).

A successful micro-co-culture model was developed and initial examination of the interactions between osteoblasts and fibroblasts in a micro-co-culturing environment was performed. Cells proliferated beyond the initial seeding region and maintained their phenotypes as indicated by ALP activity of osteoblasts and type-I collagen deposition of both cell types. The cell-to-cell cross-migration at day 2 offered a host of homotypic and heterotypic cell interactions. Micropatterning of cells offers an unique opportunity to control the local micro-environment and permit the in-depth examination of cell-cell interactions. This understanding can aid in the identification of mechanisms driving interface formation.

Seventh Set of Experiments

This set of experiments was directed to in vitro evaluations of human osteoblasts and fibroblasts co-cultured on multi-phased scaffolds. A schematic of the experimental design for the in vitro study is shown in FIG. 31-1. Phase A (meshe) was seeded with human hamstring tendon fibroblast cell suspension. Phase C was seeded with osteoblasts. Cell interaction in the interfacial Phase B was monitored over time. Acellular scaffolds served as controls.

Cell proliferation in Phases A, B, and C during 35 days of human hamstring tendon fibroblast and osteoblast co-culture on multiphased scaffolds is shown in FIG. 31-2. A general trend of increasing cell number was observed in each phase over time. Data demonstrates that all three phases of the scaffold support cellular viability and proliferation. A higher number of cells were seeded on phase A due to its inherently larger surface area compared to phase C.

Mechanical testing data for multiphased scaffolds seeded with human hamstring tendon fibroblasts and human osteoblasts over 35 days of culture (n=4) is graphically shown in FIGS. 31-3A and 31-3B. Scaffolds were tested in uniaxial compression. Compressive modulus (FIG. 31-3A) and yield strength (FIG. 31-3B) were calculated from the resulting stress-strain curves. Both cell seeded (C) and acellular (AC) scaffolds were examined at days 0, 7, 21, and 35.

Compared to the acellular controls, the cell seeded scaffolds degraded slower and better maintained their structural integrity over time. The yield strength of the acellular scaffold decreased over 35 days, while the seeded scaffolds maintained its yield strength.

Eighth Set of Experiments

Figures 3, 4, 32:
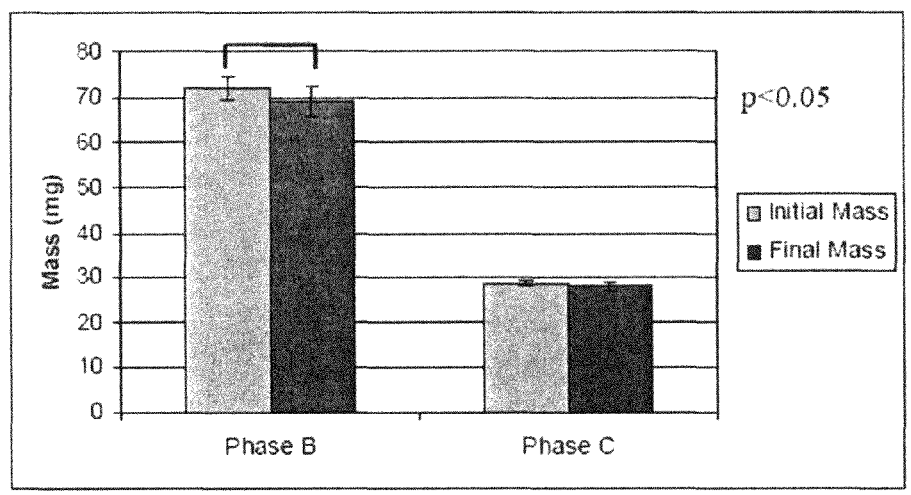

The scaffold designed for this study consisted of three phases and were fabricated in four stages (FIG. 32-1). First, Phase A was formed from polyglactin 10:90 PLGA mesh sheets (Vicryl VKML, Ethicon). Mesh sheets were cut into small segments (approximately 5 mm×5 mm) and inserted into cylindrical molds (7.44 mm diameter). Molds were heated to 150° C. for 20 hours to sinter the segments together to form a cylindrical mesh scaffold. The next phase (Phase B) consisted of 100% 85:15-poly(DL-lactide-co-glycolide) (PLAGA, Alkermes Medisorb, $M_w \approx 123.6$ kDa) microspheres formed by a water/oil/water emulsion. Briefly, 1 g PLAGA was dissolved in 10 mL methylene chloride (EM Science, Gibbstown, N.J.) and poured into a mixing 1% PVA surfactant solution (Sigma Chemicals, St. Louis, Mo.). Microspheres were mixed for 4 hours, recovered by filtration, allowed to dry in a fume hood overnight, then vacuum desiccated for 24 hours. To form the PLAGA microsphere phase, 0.075 g microspheres were inserted into the same molds as used previously, and sintered at 55° C. for 5 hours. The last phase (Phase C) consisted of composite microspheres formed from an 80:20 ratio of PLAGA and 45S5 bioactive glass (BG, MO-SCI Corporation, Rolla, Md.). Again, microspheres were formed by emulsion, except with 0.25 g bioactive glass suspended in a solution of 1 g PLAGA in 10 mL methylene chloride. Microspheres (28-30 mg/scaffold) were sintered in the same molds at 55° C. for five hours. After all three phases were sintered separately, Phases A and B were joined by methylene chloride solvent evaporation, and then sintered to Phase C for 10 hours at 55° C. in the same molds. Subsequently, scaffolds were sterilized with ethylene oxide. Final scaffold dimensions are detailed in FIGS. 32-5A and 32-5B.

Human osteoblast-like cells and hamstring tendon fibroblasts were obtained from explant culture of tissue isolated from humerus trabecular bone and hamstring tendon respectively. Trabecular bone was rinsed with PBS, then cultured in Dulbecco's Modified Eagle's Medium (DMEM, Mediatech, Herndon, Va., USA) supplemented with 10% fetal bovine serum, 1% non essential amino acids, and 1% penicillin/streptomycin (Mediatech, Herndon, Va.), and incubated at 37° C. in a 5% CO2 incubator to allow for cell migration. Hamstring tendon obtained from excess tissue utilized for hamstring tendon ACL reconstruction autografts was minced and cultured in similarly supplemented DMEM. The first migrations of cells were discarded to obtain a more uniform cell distribution. Second migration, passage 2 osteoblast-like cells and second and third migration, passage 5 hamstring tendon fibroblasts were utilized for the co-culture experiment.

Scaffold dimensions were measured prior to cell seeding and before and after EtO sterilization. Phase thickness was calculated by image analysis, while phase diameter was determined using a digital caliper. Scaffold porosity and pore diameter (Phases A and B: n=3; Phase C: n=1) were determined by mercury porosimetry (Micromeritics Autopore III and Autopore IV 9500, Micromeritics, Norcross, Ga.). The porosity data were utilized to determine cell seeding densities and cell suspension volumes for Phases A and C, with the volumes calculated such that fibroblasts suspension remains in Phase A and osteoblasts suspension in Phase C.

Hamstring tendon fibroblasts were seeded at a density of 250,000 cells/scaffold in a volume of 40.7 μL/scaffold on Phase A (FIG. 32-2). After allowing the fibroblasts to attach to the scaffolds for 20 minutes, the scaffolds were rotated upside down so that Phase C faced upwards. Subsequently, 75,000 osteoblast-like cells were seeded per scaffold in a volume of 12.5 μL. After allowing the osteoblasts to attach to the scaffold for 20 minutes, the scaffolds were covered with DMEM supplemented with 10% FBS, 1% NEAA, and 1% penicillin/streptomycin, and incubated at 37° C. and 5% $CO_2$. Ascorbic acid at a concentration of 20 μg/mL was added beginning at day 7. Media was exchanged every two days. Scaffolds were cultured in 6-well plates and covered with 7 mL of supplemented media per scaffold to minimize pH fluctuations due to rapid poly(glycolic acid) degradation.

Cell attachment, migration, and proliferation on the multiphased scaffolds were examined using SEM (5 kV, JEOL 5600LV) at days 7, 21, and 35. The scaffolds were fixed with Karnovsky's glutaraldehyde fixative, and stored at 4° C. for 24 hours. The samples were then rinsed with Hank's buffered salt solution two times, and serially dehydrated with ethanol. Cross-sections of the scaffold phases were mounted on an aluminum post and gold-coated prior to analysis.

Extracellular matrix production and mineralization were determined via histology at day 35. Scaffolds were rinsed two times with room temperature PBS. The scaffolds were then covered with 10% neutral buffered formalin and stored at 4 degrees C. Samples were plastic embedded using a modification of a procedure developed by Erben. The scaffolds were first suspended in 2% agarose (low gelling temperature, cell culture grade, Sigma, St. Louis, Mo.), then serially dehydrated with ethanol and cleared with xylene substitute (Surgipath, Sub-X, Richmond, Ill.). Following dehydration, samples were embedded in poly(methyl methacrylate) (Polysciences, Inc., Warrington, Pa.) and sectioned into 10 μm slices. The scaffold sections were stained with either hematoxylin and eosin, von Kossa or Picrosirius Red stains and imaged with light microscopy.

At days 1, 7, 21, and 35, scaffolds were rinsed twice with PBS and subsequently the three phases were separated. Each phase was then stored in 0.1% Triton-X at −80° C. Cellular proliferation in each phase was determined by means of PicoGreen DNA quantitation assay. In addition, cellular phenotype for mineralization was evaluated using a quantitative alkaline phosphatase (ALP) assay.

At days 0, 7, 21, and 35, seeded and acellular scaffolds were tested under uniaxial compression (MTS 810, n=4). The crosshead speed was 1.3 mm/min, and the scaffolds were compressed up to 35-40% strain. A 10 N preload was applied prior to testing. The effects of scaffold degradation and extracellular matrix production on scaffold compressive modulus were examined.

Mercury porosimetry data for each phase are summarized in the table shown in FIG. 32-3. Scaffold dimensions are shown in FIGS. 32-5A and 32-5B. The thickness of Phase C decreased significantly ($p<0.05$) due to contraction during the EtO sterilization (FIG. 32-5A). In addition, the thicknesses of all phases were significantly different from each other after sterilization. Scaffold diameters also varied due to contraction during sintering, in the case of Phase A, and contraction of Phase C during sterilization. The diameters of Phases B and C decreased significantly after sterilization, and the diameters of all phases were significantly different from each other after sterilization ($p<0.05$). During the scaffold fabrication process, microspheres are lost between weighing and filling the molds. This loss is mainly due to static charge accumulation in one or more of the microspheres, weighing paper, or mold, which prevents a small percentage of the microspheres from entering the molds. PLAGA-BG microspheres for Phase C generally experience a 2.1±1.4% loss in mass, while the PLAGA microspheres for Phase B suffer a loss of 4.0±1.8% (FIG. 32-4). Composite microspheres are generally more statically charged than the PLAGA microspheres; however, the stainless steel mold, used more often for the composite microspheres, dissipates charge buildup more readily than the PTFE mold, which is used more often for the PLAGA microspheres, possibly explaining why there is a significant Loss for Phase B ($p<0.05$). Mesh for Phase A is not susceptible to this loss.

Compressive modulus and yield strength were obtained for seeded and acellular control scaffolds at days 0, 7, 21, and 35 of culture. A rapid decrease in compressive modulus was observed following day 0, possibly due to rapid initial polymer degradation. By day 35, the seeded scaffolds exhibited a greater compressive modulus (FIG. 32-6A) and yield strength (FIG. 32-6B), possibly due to cellular extracellular matrix and mineralization compensating loss of scaffold strength due to polymer degradation.

In this experiment, the cell types were switched from bovine ACL fibroblasts and trabecular bone osteoblast-like cells to human hamstring tendon fibroblasts and trabecular bone osteoblasts due to the increased clinical relevance of these new cell types. This experiment aimed to acquire quantitative data about cell proliferation and migration throughout the three phases, as well as cellular alkaline phosphatase activity in each phase of the scaffold.

Based on the previous experiment performed with bovine cells, it is apparent that the biomimetic, multi-phased scaffolds support the growth and ECM production of both osteoblasts and fibroblasts. After 28 days of culture, collagen production was evident in all three phases and mineralized matrix was found in the bone and interface regions. Osteoblast and fibroblast interaction at the interface (Phase B) suggests that these cells may play a significant role in the development of a functional insertion site. These findings demonstrate that this novel scaffold is capable of simultaneously supporting the growth of multiple cell types and can be used as a model system to regenerate the soft tissue to bone interface. Additional studies can focus on scaffold optimization and the development of the interface on the novel scaffold.

Ninth Set of Experiments

The objective of the set of experiments was to incorporate electrospun PLAGA meshes into the multi-phased scaffold design, substituting the Ethicon mesh phase, and allowing the entire scaffold to be made in-house.

Electrospinning, short for electrostatic spinning, is a relatively new term that describes a principle first discovered in the first half of the $20^{th}$ century (see, for example, U.S. Pat. Nos. 1,975,504, 2,160,962, 2,187,306, 2,323,025 and 2,349,950 to Formhals, the entire contents of which are incorporated herein by reference). Electrostatic spinning involves the fabrication of fibers by applying a high electric potential to a polymer solution. The material to be electrospun, or dissolved into a solution in the case of polymers, is loaded into a syringe or spoon, and a high potential is applied between the solution and a grounded substrate. As the potential is increased, the electrostatic force applied to the polymer solution overcomes surface tension, distorting the solution droplet into a Taylor cone from which a jet of solution is ejected toward the grounded plate. The jet splays into randomly oriented fibers, assuming that the solution has a high cohesive strength, linked to polymer chain molecular weight, to prevent droplets from forming instead of fibers in a process known as electrospraying. These fibers have diameters ranging from nanometer scale to greater than 1 μm and are deposited onto the grounded substrate or onto objects inserted into the electric field forming a non-woven mesh. Mesh characteristics can be customized by altering electrospinning parameters. For example, fiber diameter and morphology can be altered, including the formation of beads along the fibers, by controlling applied voltage and polymer solution surface tension and viscosity. Also, fiber orientation can be controlled by rotating the grounded substrate. This high degree of customizability and ability to use many different materials, such as biodegradable polymers and silks, grant this fabrication method a high potential in the development of materials for biomedical application. Management of fiber diameter allows surface area to be controlled, and polymers with different degradation rates can be combined in various ratios to control fiber degradation, both of which are significant in drug delivery applications. Also, controlling the orientation of fiber deposition grants a degree of control over cell attachment and migration. Moreover, the ability to electrospin fiber meshes onto non-metal objects placed in the electric field enables the fabrication of multiphasic scaffold systems.

Here, in order to obtain precise parameters for the mesh fibers, including fiber diameter, morphology, and alignment, the effects of processing parameters on fiber characteristics were studied. A variable-speed rotating drum was designed and constructed to serve as a substrate for aligned fibers, and rheological experiments were performed on the polymer solutions to determine the effect of polymer concentration on solution viscosity and the subsequent effect of solution viscosity on fiber diameter and morphology.

In addition to determining the speed of each gear, the effect of each speed on fiber alignment was determined qualitatively. A 30% v/v PLAGA solution was prepared with 60% dimethylformamide and 10% ethanol, and this solution was electrospun onto the rotating drum at each of the four speed settings. The resulting meshes were examined by scanning electron microscopy (JEOL 5600LV).

The relationship between polymer concentration (Alkermes 85:15 PLAGA) and solution viscosity was determine by means of a rheological study. Three concentrations of polymer were tested—20%, 30%, and 40% v/v—in dimethylformamide (DMF) and ethanol. The composition of each solution is listed in the table shown in FIG. 33-1. Solutions were analyzed using an Advanced Rheometer AR 2000t. There was variability in the viscosity measurements (n=1) at different strain rates due to the evaporation of solvent during testing. The geometry used for the viscosity measurements was a 25 mm stainless steel disc. A solvent trap was not used since it is not designed to fit with this geometry and a prior trial using the solvent trap with another geometry resulted in poor results, possibly because water from the solvent trap seal interacted with the polymer solution. Additional trials can use a solvent trap to obtain consistent and reliable values for viscosity. For the present study, averages were taken of the viscosity measurements taken at strain rates tested after the equipment had equilibrated. As a result, there are standard deviations for the viscosity measurements even with an n of 1.

The surface velocity of the rotating drum was seen to increase with increased pulley positions from gear 1 to gear 4 (see the table shown in FIG. 33-2). The degree of fiber alignment increased with increasing drum velocity, as seen in the SEMS of each mesh (see FIGS. 33-3A through 33-3D).

It was found that (as expected) the degree of fiber orientation increased with increasing drum rotational velocity. The image was analyzed and a histogram of fiber angles was generated against the horizontal axis of the image at regular interval across the image. Thus, the degree of alignment of the fibers can be quantified. It is desirable to control the degree of fiber alignment in the electrospun meshes so that the extracellular environment found at the interface can be mimicked. By producing biomimetic scaffolds, it was intended to direct cell growth to reproduce the tissue inhomogeneity found at the native ACL insertions. In addition to controlling the fiber alignment, it is desirable to control fiber diameter and morphology. It was previously determined that substituting 10% of the DMF in the polymer solutions with ethanol reduces the surface tension of the solution and results in a significant reduction in the number of beads formed along the fibers when electrospinning PLAGA. This effect was also observed by Fong et al., who reduced the number of beads in electrospun poly(ethylene oxide) (PEO) meshes by the addition of ethanol. Surface tension of the polymer solution acts to form spheres during the electrospinning process. By reducing the solution surface tension, the formation of spheres is less favorable and straighter fibers result. Fong et al. also determined that the addition of ethanol increased the viscosity of the PEO:water solutions, which also favors the formation of straight fibers, and results in increased fiber diameter. Deitzel et al. also have demonstrated a relationship between PEO:water solution viscosity and fiber diameter, with fiber diameter increasing with increasing viscosity according to a power law. A relationship between solution viscosity and concentration of polymer can be determined in order to understand how PLAGA:N,N-DMF viscosity affects fiber diameter and morphology. The effect of solution viscosity on fiber diameter and morphology can be determined by spinning the various solutions and examining the resulting meshes by SEM. Other variables can affect the fiber parameters. By changing the percentage of polymer, the surface tensions of the polymer solutions also change in addition to the viscosity. Therefore, in addition to testing the viscosities of each solution, the surface tension of each solution are measured. It is desirable to keep all variables constant except for viscosity in order to truly determine the effect of solution viscosity on fiber characteristics. However, the interrelation of many of the electrospinning parameters complicates the process.

A PLAGA mesh was electrospun directly onto a microsphere scaffold. This is one way to incorporate the mesh. In addition, the scaffolds can be secured to the drum and aligned fibers electrospin directly onto the scaffolds. However, because of the high rotational velocities, it is difficult to secure the scaffolds and prevent them from flying off the drum when it begins rotating. Alternatively, aligned fiber meshes can simply be spun separately, and then later sintered to the microsphere scaffolds. For example, aligned fiber meshes can be electrospun onto aluminum foil, then wrapped around a rod with multiple mesh sheets sintered together to obtain a hollow cylinder of aligned fibers.

FIG. 33-4A and 33-4B show scanning electron microscopy (SEM) images of another embodiment of multi-phased scaffold, with 85:15 PLAGA electrospun mesh joined with PLAGA:BG composite microspheres.

REFERENCES

1. Abate, J. A., Fadale, P. D., Hulstyn, M. J. & Walsh, W. R., "Initial fixation strength of polylactic acid interference screws in anterior cruciate ligament reconstruction," Arthroscopy 14, 278-284 (1998).
2. Allum, R. L., "BASK Instructional Lecture 1: graft selection in anterior cruciate ligament reconstruction," Knee 8, 69-72 (2001).
3. Altman, G. H., et al. "Advanced bioreactor with controlled application of multi-dimensional strain for tissue engineering," Journal of Biomechanical Engineering 124, 742-749 (2002).
4. Altman, G. H., et al., "Silk matrix for tissue engineered anterior cruciate ligaments," Biomaterials 23, 4131-4141 (2002).
5. American Academy of Orthopaedic Surgeons, "Arthoplasty and Total Joint Replacement Procedures: United States 1990 to 1997," (Report, United States) (1997).
6. Anderson, K. et al., "Augmentation of tendon healing in an intraarticular bone tunnel with use of a bone growth factor," Am. J. Sports Med. 29, 689-698 (2001).
7. Batycky, R. P., Hanes, J., Langer, R. & Edwards, D. A., "A theoretical model of erosion and macromolecular drug release from biodegrading microspheres," J. Pharmaceutical Sciences 86, 1464-1477 (1997).
8. Bellincampi, L. D., Closkey, R. F., Prasad, R., Zawadsky, J. P. & Dunn, M. G., "Viability of fibroblast-seeded ligament analogs after autogenous implantation," J. Orthop. Res. 16, 414-420 (1998).
9. Benjamin, M., Evans, E. J., Rao, R. D., Findlay, J. A. & Pemberton, D. J., "Quantitative differences in the histology of the attachment zones of the meniscal horns in the knee joint of man," J. Anat. 177, 127-134 (1991).
10. Berg, E. E., "Autograft bone-patella tendon-bone plug comminution with loss of ligament fixation and stability," Arthroscopy 12, 232-235 (1996).
11. Beynnon, B. et al., "A sagittal plane model of the knee and cruciate ligaments with application of a sensitivity analysis," J. Biomech. Eng. 118, 227-239 (1996).
12. Beynnon, B. D. et al., "The effect of functional knee bracing on the anterior cruciate ligament in the weightbearing and nonweightbearing knee," Am. J. Sports Med. 25, 353-359 (1997).
13. Blickenstaff, K. R., Grana, W. A. & Egle, D., "Analysis of a semitendinosus autograft in a rabbit model," Am. J. Sports Med. 25, 554-559 (1997).
14. Bolton, C. W. & Bruchman, W. C., "The GORE-TEX expanded polytetrafluoroethylene prosthetic ligament. An in vitro and in vivo evaluation," Clin. Orthop. 202-213 (1985).
15. Borden, M., Attawia, M., Khan, Y. & Laurencin, C. T. Tissue engineered microsphere-based matrices for bone repair: design and evaluation. Biomaterials 23, 551-559 (2002).
16. Bonfield, W., "Composites for bone replacement," J. Biomed. Eng. 10, 522-526 (1988).
17. Boskey, A. L. et al., "The mechanism of beta-glycerophosphate action in mineralizing chick limb-bud mesenchymal cell cultures," J. Bone Min. Res. 11, 1694-1702 (1996).
18. Brand, J., Jr., Weiler, A., Caborn, D. N., Brown, C. H., Jr. & Johnson, D. L., "Graft fixation in cruciate ligament reconstruction," Am. J. Sports Med. 28, 761-774 (2000).
19. Brody, G. A., Eisinger, M., Arnoczky, S. P. & Warren, R. F., "In vitro fibroblast seeding of prosthetic anterior cruciate ligaments. A preliminary study," Am. J. Sports Med. 16, 203-208 (1988).
20. Bromage, T. G., Smolyar, I., Doty, S. B., Holton, E. & Zuyev, A. N., "Bone growth rate and relative mineralization density during space flight," Scanning 20, 238-239 (1998).
21. Burkart, A., Imhoff, A. B. & Roscher, E., "Foreign-body reaction to the bioabsorbable suretac device," Arthroscopy 16, 91-95 (2000).
22. Butler, D. L., Goldstein, S. A. & Guilak, F., "Functional tissue engineering: the role of biomechanics," J. Biomech. Eng. 122, 570-575 (2000).
23. Chen, C. H. et al., "Enveloping the tendon graft with periosteum to enhance tendon-bone healing in a bone tunnel: A biomechanical and histologic study in rabbits," Arthroscopy 19, 290-296 (2003).
24. Cheung, H. S. & McCarty, D. J., "Mitogenesis induced by calcium-containing crystals. Role of intracellular dissolution," Exp. Cell Res. 157, 63-70 (1985).
25. Clark, J. M. & Sidles, J. A., "The interrelation of fiber bundles in the anterior cruciate ligament," J. Orthop. Res. 8, 180-188 (1990).
26. Cooper, J. A., "Design, optimization and in vivo evaluation of a tissue-engineered anterior cruciate ligament replacement," Drexel University (Thesis/Dissertation) (2002).
27. Cooper, J. A., Lu, H. H. & Laurencin, C. T., "Fiber-based tissue engineering scaffold for ligament replacement: design considerations and in vitro evaluation," Proceedings of 5th World Biomaterial Congress, 208 (Abstract) (2000).
28. Daniel, D. M. et al., "Fate of the ACL-injured patient. A prospective outcome study," Am. J. Sports Med. 22, 632-644 (1994).
29. Deitzel et al., *Polymer* 42, (2001).

30. Deitzel et al., *Polymer* 43, (2002).
31. Ducheyne, P., "Bioceramics: material characteristics versus in vivo behavior," J. Biomed. Matls. Res. 21, 219-236 (1987).
32. Dunn, M. G., Liesch, J. B., Tiku, M. L., Maxian, S. H. & Zawadsky, J. P., "The Tissue Engineering Approach to Ligament Reconstruction," Matls. Res. Soc. 331, 13-18 (1994).
33. El-Amin, S. F. et al., "Human osteoblast integrin expression on degradable polymeric materials for tissue engineered bone," J. Orthop. Res. (In Press) (2001).
34. Erben, *J. Histochem. Cytochem.* 45, 307-314 (1997).
35. Fleming, B. C., Abate, J. A., Peura, G. D. & Beynnon, B. D., "The relationship between graft tensioning and the anterior-posterior laxity in the anterior cruciate ligament reconstructed goat knee," J. Orthop. Res. 19, 841-844 (2001).
36. Fleming, B., Beynnon, B., Howe, J., McLeod, W. & Pope, M., "Effect of tension and placement of a prosthetic anterior cruciate ligament on the anteroposterior laxity of the knee," J. Orthop. Res. 10, 177-186 (1992).
37. Fong et al., *Polymer*, (1999).
38. Fridrikh et al., *PhysRevLet* (2003).
39. Fu, F. H., Bennett, C. H., Ma, C. B., Menetrey, J. & Lattermann, C., "Current trends in anterior cruciate ligament reconstruction. Part II. Operative procedures and clinical correlations," Am. J. Sports Med. 28, 124 130 (2000).
40. Fujikawa, K., Iseki, F. & Seedhom, B. B., "Arthroscopy after anterior cruciate reconstruction with the Leeds-Keio ligament," J. Bone Joint Surg. Br. 71, 566-570 (1989).
41. Gao, J. & Messner, K., "Quantitative comparison of soft tissue-bone interface at chondral ligament insertions in the rabbit knee joint," J. Anat. 188, 367-373 (1996).
42. Gao, J., Rasanen, T., Persliden, J. & Messner, K., "The morphology of ligament insertions after failure at low strain velocity: an evaluation of ligament entheses in the rabbit knee," J. Anat. 189, 127-133 (1996).
43. Gotlin, R. S. & Huie, G., "Anterior cruciate ligament injuries. Operative and rehabilitative options," Phys. Med. Rehabil. Clin. N. Am. 11, 895-928 (2000).
44. Goulet, F. et al., "Principles of Tissue Engineering," Lanza, R. P., Langer, R. & Vacanti, J. P. (eds.), pp. 639-645 Academic Press (2000).
45. Grana, W. A., Egle, D. M., Mahnken, R. & Goodhart, C. W., "An analysis of autograft fixation after anterior cruciate ligament reconstruction in a rabbit model," Am. J. Sports Med. 22, 344-351 (1994).
46. Gregoire, M., Orly, I., Kerebel, L. M. & Kerebel, B., "In vitro effects of calcium phosphate biomaterials on fibroblastic cell behavior," Biol. Cell 59, 255-260 (1987).
47. Harner, C. D. et al., "Quantitative analysis of human cruciate ligament insertions," Arthroscopy 15, 741-749 (1999).
48. Hench, L. L., "Bioceramics: from concept to clinic," J. Am. Cera. Soc. 74(7), 1487-1510 (1991).
49. Jackson, D. W., American Academy of Orthopaedic Surgeon Bulletin 40, 10-11 (1992).
50. Jackson, D. W., Grood, E. S., Arnoczky, S. P., Butler, D. L. & Simon, T. M., "Cruciate reconstruction using freeze dried anterior cruciate ligament allograft and a ligament augmentation device (LAD). An experimental study in a goat model," Am. J. Sports Med. 15, 528-538 (1987).
51. Jackson, D. W. et al., Trans. Orhtop. Res. Soc. 16, 208 (Abstract)(1991).
52. Jackson, D. W. et al., "A comparison of patellar tendon autograft and allograft used for anterior cruciate ligament reconstruction in the goat model," Am. J. Sports Med. 21, 176-185 (1993).
53. Jiang, J., Nicoll, S. B. & Lu, H. H., "Effects of Osteoblast and Chondrocyte Co-Culture on Chondrogenic and Osteoblastic Phenotype In Vitro," Trans. Orhtop. Res. Soc. 49 (Abstract) (2003).
54. Johnson, R. J., "The anterior cruciate: a dilemma in sports medicine," Int. J. Sports Med. 3, 71-79 (1982).
55. Kim et al., *Biomaterials* (2003).
56. Kurosaka, M., Yoshiya, S. & Andrish, J. T., "A biomechanical comparison of different surgical techniques of graft fixation in anterior cruciate ligament reconstruction," Am. J Sports Med. 15, 225-229 (1987).
57. Kurzweil, P. R., Frogameni, A. D. & Jackson, D. W., "Tibial interference screw removal following anterior cruciate ligament reconstruction," Arthroscopy 11, 289-291 (1995).
58. Larson, R. P., "The Crucial Ligaments: Diagnosis and Treatment of Ligamentous Injuries About the Knee," John, A. Jr. & Feagin, J. A. (eds.), pp. 785-796 Churchill Livingstone, New York (1994).
59. Liu, S. H. et al., "Morphology and matrix composition during early tendon to bone healing," Clinical Orthopaedics & Related. Research. 253-260 (1997).
60. Loh, J. C. et al., "Knee stability and graft function following anterior cruciate ligament reconstruction: Comparison between 11 o'clock and 10 o'clock femoral tunnel placement," Arthroscopy 19, 297-304 (2003).
61. Lu, H. H., Pollack, S. R. & Ducheyne, P., "Temporal zeta potential variations of 45S5 bioactive glass immersed in an electrolyte solution," J. Biomed. Matls. Res. 51, 80-87 (2000).
62. Lu, H. H., Pollack, S. R. & Ducheyne, P., "45S5 bioactive glass surface charge variations and the formation of a surface calcium phosphate layer in a solution containing fibronectin," J. Biomed. Matls. Res. 54, 454-461 (2001).
63. Lu, H. H., Cooper, J. A., Ko, F. A., Attawia, M. A. & Laurencin, C. T., "Effect of polymer scaffold composition on the morphology and growth of anterior cruciate ligaments cells," Society for Biomaterials Proceedings (Abstract) (2001).
64. Lu, H. H., El Amin, S. F., Scott, K. D. & Laurencin, C. T., "Three dimensional, bioactive, biodegradable, polymer bioactive glass composite scaffolds with improved mechanical properties support collagen synthesis and mineralization of human osteoblast-like cells in vitro," J. Biomed. Matls. Res. 64A, 465-474 (2003).
65. Lu, H. H. et al., "Evaluation of Optimal Parameters in the Co-Culture of Human Anterior Cruciate Ligament Fibroblasts and Osteoblasts for Interface Tissue Engineering," ASME 2003 Summer Bioengineering Conference (Abstract) (2003).
66. Markolf, K. L. et al., "Effects of femoral tunnel placement on knee laxity and forces in an anterior cruciate ligament graft," J. Orthop. Res. 20, 1016-1024 (2002).
67. Matthews, L. S., Soffer, S. R., "Pitfalls in the use of interference screws for anterior cruciate ligament reconstruction: brief report," Arthroscopy 5, 225-226 (1989).
68. Matyas, J. R., Anton, M. G., Shrive, N. G. & Frank, C. B., "Stress governs tissue phenotype at the femoral insertion of the rabbit MCL," J. Biomech. 28, 147-157 (1995).
69. McCarthy, D. M., Tolin, B. S., Schwendeman, L., Friedman, M. J. & Woo, S. L., "The Anterior Cruciate Ligament: Current and Future Concepts," Douglas, W. & MD Jackson (eds.) Raven Press, New York (1993).

70. Messner, K., "Postnatal development of the cruciate ligament insertions in the rat knee. Morphological evaluation and immunohistochemical study of collagens types I and II," Acta Anatomica 160, 261-268 (1997).
71. Moore, P. B. & Dedman, J. R., "Calcium binding proteins and cellular regulation," Life Sci. 31, 2937-2946 (1982).
72. Nicoll, S. B., Wedrychowska, A., Smith, N. R. & Bhatnagar, R. S., "Modulation of proteoglycan and collagen profiles in human dermal fibroblasts by high density micromass culture and treatment with lactic acid suggests change to a chondrogenic phenotype," Connect. Tissue Res. 42, 59-69 (2001).
73. Niyibizi, C., Sagarrigo, V. C., Gibson, G. & Kavalkovich, K., "Identification and immunolocalization of type X collagen at the ligament-bone interface," Biochem. Biophys. Res. Commun. 222, 584-589 (1996).
74. Noyes, F. R. & Barber-Westin, S. D., "Revision anterior cruciate ligament surgery: experience from Cincinnati," Clin. Orthop. 116-129 (1996).
75. Noyes, F. R., Mangine, R. E. & Barber, S., "Early knee motion after open and arthroscopic anterior cruciate ligament reconstruction," Am. J. Sports Med. 15, 149-160 (1987).
76. Panni, A. S., Milano, G., Lucania, L. & Fabbriciani, C., "Graft healing after anterior cruciate ligament reconstruction in rabbits," Clin. Orthop. 203-212 (1997).
77. Pena, F., Grontvedt, T., Brown, G. A., Aune, A. K. & Engebretsen, L., "Comparison of failure strength between metallic and absorbable interference screws. Influence of insertion torque, tunnel-bone block gap, bone mineral density, and interference," Am. J. Sports Med. 24, 329-334 (1996).
78. Petersen, W. & Tillmann, B., "Structure and vascularization of the cruciate ligaments of the human knee joint," Anat. Embryol. (Berl) 200, 325-334 (1999).
79. Robertson, D. B., Daniel, D. M. & Biden, E., "Soft tissue fixation to bone," Am. J. Sports Med. 14, 398-403 (1986).
80. Rodeo, S. A., Suzuki, K., Deng, X. H., Wozney, J. & Warren, R. F., "Use of recombinant human bone morphogenetic protein-2 to enhance tendon healing in a bone tunnel," Am. J. Sports Med. 27, 476-488 (1999).
81. Rodeo, S. A., Arnoczky, S. P., Torzilli, P. A., Hidaka, C. & Warren, R. F., "Tendon-healing in a bone tunnel. A biomechanical and histological study in the dog," J. Bone Joint Surg. Am. 75, 1795-1803 (1993).
82. Safran, M. R. & Harner, C. D., "Technical considerations of revision anterior cruciate ligament surgery," Clin. Orthop. 50-64 (1996).
83. Sagarriga, V. C., Kavalkovich, K., Wu, J. & Niyibizi, C., "Biochemical analysis of collagens at the ligament-bone interface reveals presence of cartilage-specific collagens," Arch. Biochem. Biophys. 328, 135-142 (1996).
84. Scapinelli, R. & Little, K., "Observations on the mechanically induced differentiation of cartilage from fibrous connective tissue," J. Pathol. 101, 85-91 (1970).
85. Schafer, et al., "In vitro generation of osteochondral composites," Biomaterials 21:2599-2606 (2000).
86. Schafer, et al., "Tissue-engineered composites for the repair of large osteochondral defects," Arthritis Rheum. 46:2524-2534 (2002).
87. Shellock, F. G., Mink, J. H., Curtin, S. & Friedman, M. J., "MR imaging and metallic implants for anterior cruciate ligament reconstruction: assessment of ferromagnetism and artifact," J. Magn. Reson. Imaging 2, 225-228 (1992).
88. Shin et al., *Polymer* 42, (2001).
89. Sittinger, et al., "Engineering of cartilage tissue using bieresorbable polymer carriers in perusion culture," Biomaterials 15(6):451-456 (1994).
90. Spalazzi, J. P., Dionisio, K. L., Jiang, J. & Lu, H. H., "Chondrocyte and Osteoblast Interaction on a Degradable Polymer Ceramic Scaffold," ASME 2003 Summer Bioengineering Conference (Abstract) (2003).
91. Steiner, M. E., Hecker, A. T., Brown, C. H., Jr. & Hayes, W. C., "Anterior cruciate ligament graft fixation. Comparison of hamstring and patellar tendon grafts," Am. J. Sports Med. 22, 240-246 (1994).
92. Thomas, N. P., Turner, I. G. & Jones, C. B., "Prosthetic anterior cruciate ligaments in the rabbit. A comparison of four types of replacement," J. Bone Joint Surg. Br. 69, 312-316 (1987).
93. Thomopoulos, S. et al., "The localized expression of extracellular matrix components in healing tendon insertion sites: an in situ hybridization study," J. Orthop. Res. 20, 454-463 (2002).
94. Wei, X. & Messner, K., "The postnatal development of the insertions of the medial collateral ligament in the rat knee," Anat. Embryol. (Berl) 193, 53-59 (1996).
95. Weiler, A., Hoffmann, R. F., Bail, H. J., Rehm, O. & Sudkamp, N. P., "Tendon healing in a bone tunnel. Part II: Histologic analysis after biodegradable interference fit fixation in a model of anterior cruciate ligament reconstruction in sheep," Arthroscopy 18, 124-135 (2002).
96. Weiler, A., Windhagen, H. J., Raschke, M. J., Laumeyer, A. & Hoffmann, R. F., "Biodegradable interference screw fixation exhibits pull-out force and stiffness similar to titanium screws," Am. J. Sports Med. 26, 119-126 (1998).
97. Woo, S. L., Gomez, M. A., Seguchi, Y., Endo, C. M. & Akeson, W. H., "Measurement of mechanical properties of ligament substance from a bone-ligament-bone preparation," J. Orthop. Res. 1, 22-29 (1983).
98. Woo, S. L., Newton, P. O., MacKenna, D. A. & Lyon, R. M., "A comparative evaluation of the mechanical properties of the rabbit medial collateral and anterior cruciate ligaments," J. Biomech. 25, 377-386 (1992).
99. Wu H. et al., J. Am. Chem. Soc. 2003 Jan. 15; 125(2):554-559.
100. Wuthier, R. E., "Involvement of cellular metabolism of calcium and phosphate in calcification of avian growth plate cartilage," J. Nutr. 123, 301-309 (1993).
101. Xu et al., *Biomaterials* 25, 877-886, (2004).
102. Yahia, L., "Ligaments and Ligamentoplasties," Springer Verlag, Berlin Heidelberg (1997).
103. Yoshiya, S., Nagano, M., Kurosaka, M., Muratsu, H. & Mizuno, K., "Graft healing in the bone tunnel in anterior cruciate ligament reconstruction," Clin. Orthop. 278-286 (2000).

What is claimed is:

1. A scaffold apparatus for musculoskeletal tissue engineering, said apparatus comprising three or more phases, a first end designed to promote growth and maintenance of bone tissue and a second end opposite the first end designed to promote growth and maintenance of a tissue which is other than bone tissue, wherein at least one of the three or more phases comprises a porous fiber mesh formed from degradable electrospun polymer fiber.

2. The scaffold apparatus of claim 1, wherein the scaffold apparatus promotes growth and maintenance of soft tissue and bone.

3. A scaffold apparatus for soft tissue-to-bone interface tissue engineering comprising:
a first region comprising composite microspheres of a first size and composition optimized to promote growth, proliferation, and differentiation of a first cell type for integration and growth of bone;

a second region joined to the first region, said second region comprising microspheres and/or a fibrous mesh, said microspheres and/or fibrous mesh having a second size and a second composition;

a third region joined to the second region, said third region comprising microspheres and/or a fibrous mesh, said microspheres and/or fibrous mesh having a third size and a third composition, and said second and third regions being optimized to promote growth, proliferation and differentiation of a second cell type for integration and formation of a first soft tissue and/or bone; and a fourth region joined to the third region, said fourth region comprising microspheres and/or a fibrous mesh, said microspheres and/or fibrous mesh having a composition adapted to promote growth, proliferation, and differentiation of a third cell type for integration and growth of a second soft tissue and/or bone.

4. The scaffold apparatus of claim 3, wherein said first, second, third and fourth regions are joined together through one of a solid state sintering process and a solvent aggregation process, in which selected growth factors or bioactive agents are incorporated into each region to promote formation, growth and integration of bone and said first and second soft tissues.

5. The scaffold apparatus of claim 3, wherein said composite microspheres of said first region include a range of sizes.

6. The scaffold apparatus of claim 3, wherein said microspheres and/or fibrous mesh of said second region include a range of sizes.

7. The scaffold apparatus of claim 3, wherein said microspheres and/or fibrous mesh of said second region include a gradient of sizes.

8. The scaffold apparatus of claim 3, wherein said microspheres and/or fibrous mesh of said second region include a gradient of compositions.

9. The scaffold apparatus of claim 3, wherein said microspheres and/or fibrous mesh of said third region include a range of sizes.

10. The scaffold apparatus of claim 3, wherein said microspheres and/or fibrous mesh of said third region include a gradient of sizes.

11. The scaffold apparatus of claim 3, wherein said microspheres and/or fibrous mesh of said third region include a gradient of compositions.

12. The scaffold apparatus of claim 3, wherein said fibrous mesh is electrospun.

13. The scaffold apparatus of claim 3, wherein said scaffold apparatus is integrated in a graft collar.

* * * * *